US012753186B2

(12) United States Patent
Shin et al.

(10) Patent No.: US 12,753,186 B2
(45) Date of Patent: Oct. 6, 2026

(54) COMPOUND AND COMPOSITION FOR PREVENTING OR TREATING NEUROINFLAMMATORY BRAIN DISEASES COMPRISING SAME AS ACTIVE INGREDIENT

(71) Applicant: KOREA INSTITUTE OF OCEAN SCIENCE & TECHNOLOGY, Busan (KR)

(72) Inventors: Hee Jae Shin, Busan (KR); Byeoung Kyu Choi, Chungcheongnam-do (KR); Hwa Sun Lee, Gyeonggi-do (KR)

(73) Assignee: Korea Institute of Ocean Science & Technology, Busan (KR)

( * ) Notice: Subject to any disclaimer, the term of this patent is extended or adjusted under 35 U.S.C. 154(b) by 320 days.

(21) Appl. No.: 18/705,508

(22) PCT Filed: Dec. 15, 2021

(86) PCT No.: PCT/KR2021/019061

§ 371 (c)(1),
(2) Date: Apr. 26, 2024

(87) PCT Pub. No.: WO2023/075016

PCT Pub. Date: May 4, 2023

(65) Prior Publication Data

US 2025/0034164 A1 Jan. 30, 2025

(30) Foreign Application Priority Data

Oct. 28, 2021 (KR) ........................ 10-2021-0146019

(51) Int. Cl.

*C07D 493/08* (2006.01)
*A61K 31/352* (2006.01)
*A61P 25/16* (2006.01)

(52) U.S. Cl.

CPC .......... *C07D 493/08* (2013.01); *A61K 31/352* (2013.01); *A61P 25/16* (2018.01)

(58) Field of Classification Search

CPC .................................................... C07D 493/08
See application file for complete search history.

(56) References Cited

FOREIGN PATENT DOCUMENTS

| | | | |
|---|---|---|---|
| CN | 108660169 | | 10/2018 |
| JP | 1988190888 | A | 8/1988 |
| KR | 20210109733 | A | 9/2021 |

OTHER PUBLICATIONS

Extended European Search Report for Application No. EP 21962639.7 mailed Sep. 24, 2025.

Jin Ying et al., "Amycolasporins and Dibenzoyls from Lichen-Associated Amycolatopsis hippodromi and Their Antibacterial and Anti-inflammatory Activities", Journal of Natural Products, vol. 83, No. 12, Nov. 20, 2020, pp. 3545-3553.

Shan et al., "Macranthoside B induces apoptosis and autophagy via reactive oxygen species accumulation in human ovarian cancer A2780 cells", Nutrition and Cancer, DOI: 10.1080/01635581.2016.1142587.

International Search Report for corresponding PCT Application No. PCT/KR2021/019061 mailed Jul. 22, 2022.

Cui et al., "Echinosporins as new cell cycle inhibitors and apoptosis inducers from marine-derived Streptomyces albogriseolus", Fitoterapia 78 (2007) 238-240.

Lankapalli et al., "Interaction of Marine Streptomyces Compounds with Selected Cancer Drug Target Proteins by in silico Molecular Docking Studies", Interdiscip Sci Comput Life Sci (2013) 5: 37-44, DOI: 10.1007/s12539-013-0146-0.

Shin, H.J. et al. A new inhibitor of microglial neurotoxicity from marine derived *Streptomyces* species, Journal of pharmacognosy and natural products: fu international conference and exhibition on marine drugs and natural products. Jul. 25-27, 2016, p. I.

*Primary Examiner* — Golam M Shameem

(74) *Attorney, Agent, or Firm* — Wood, Phillips, Katz, Clark & Mortimer

(57) ABSTRACT

The present invention relates to a novel compound and a composition for preventing or treating neuroinflammatory brain diseases, the composition comprising same as an active ingredient and, more specifically, to a pharmaceutical composition for preventing or treating neuroinflammatory brain diseases and a food composition for preventing or ameliorating neuroinflammatory brain diseases, the compositions comprising a compound represented by Chemical Formula 1 as an active ingredient. The novel compound of the present invention can be effectively used to provide a therapeutic agent for preventing or treating neuroinflammatory brain diseases, a food for ameliorating neuroinflammatory brain diseases, or a functional food for enhancing a cognitive function.

7 Claims, 22 Drawing Sheets

【Fig 1】
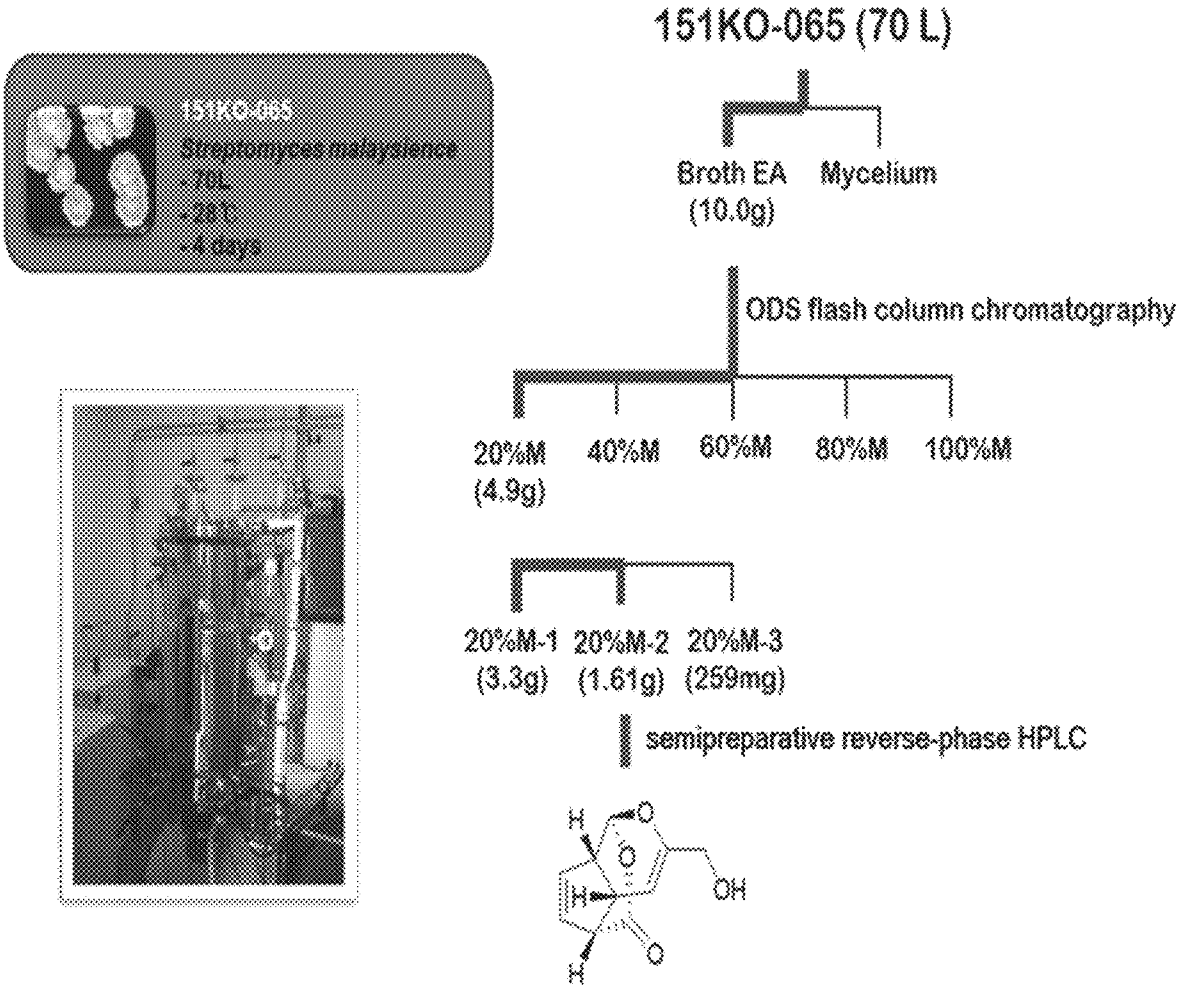

【Fig 2】
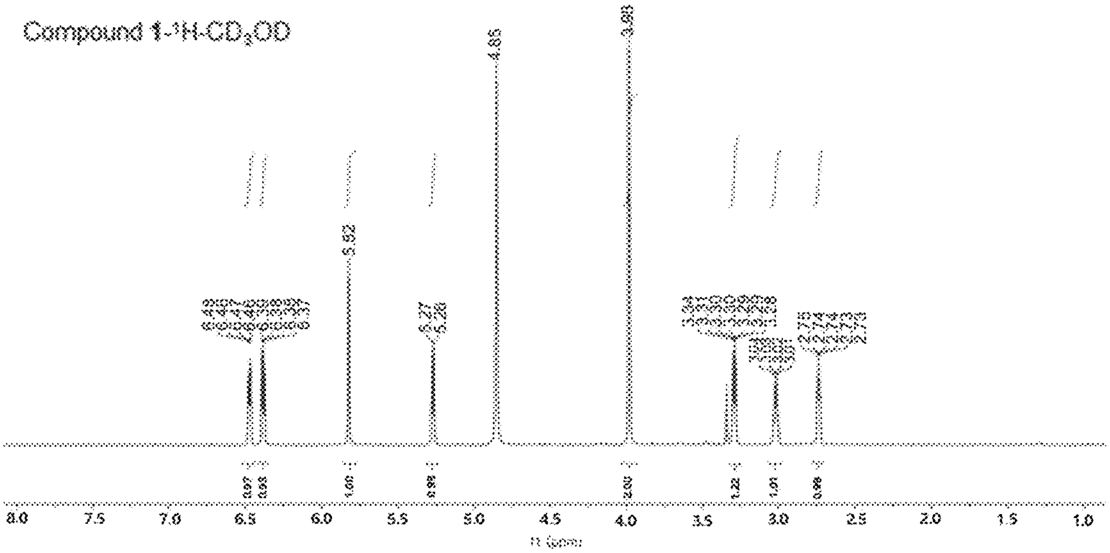
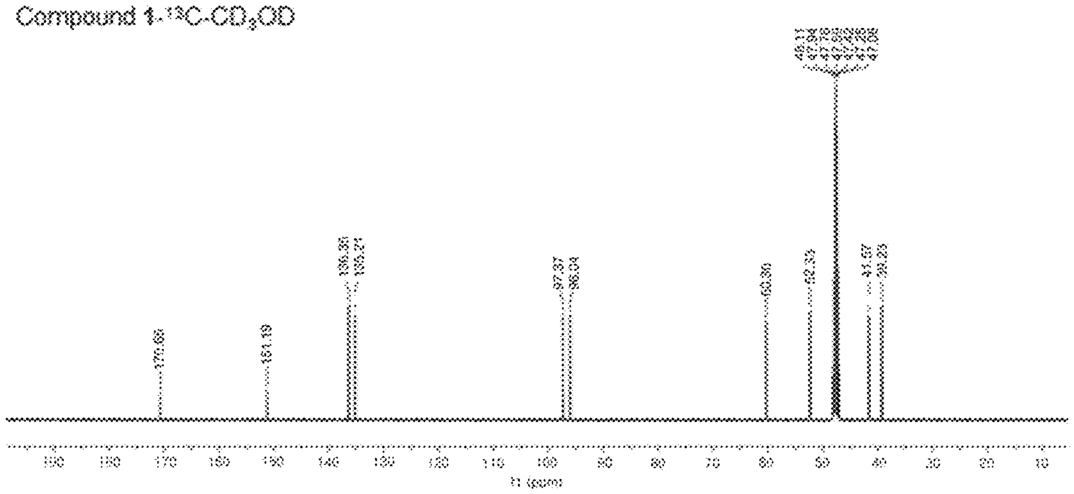

【Fig 3】

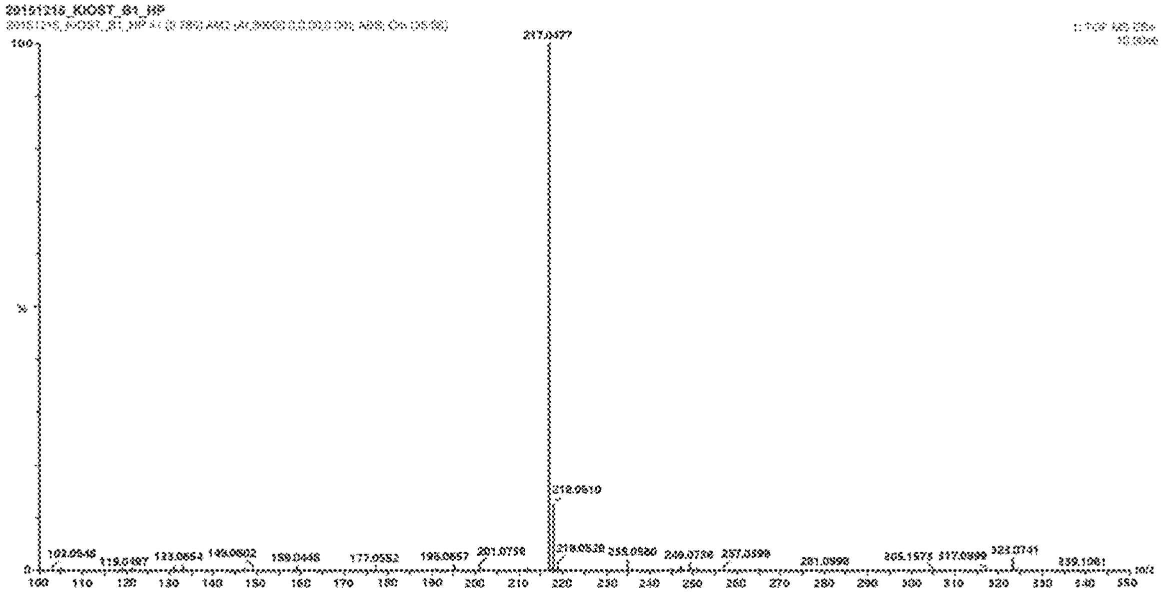

Elemental Composition Report

Single Mass Analysis
Tolerance = 5.0 PPM / DBE: min = -1.5, max = 50.0
Element prediction: Off
Number of isotope peaks used for i-FIT = 3

Monoisotopic Mass, Even Electron Ions
16 formula(e) evaluated with 1 results within limits (up to 20 best isotopic matches for each mass)
Elements Used:
C: 1-20 H: 1-20 O: 1-5 Na: 0-1

| | | | | | | | | |
|---|---|---|---|---|---|---|---|---|
| Minimum: | | | | -1.5 | | | | |
| Maximum: | | 5.0 | 5.0 | 50.0 | | | | |
| Mass | Calc. Mass | mDa | PPM | DBE | i-FIT | Norm | Conf(%) | Formula |
| 217.0477 | 217.0477 | 0.0 | 0.0 | 5.5 | 1313.8 | n/a | n/a | C10 H10 O4 Na |

【Fig 4】

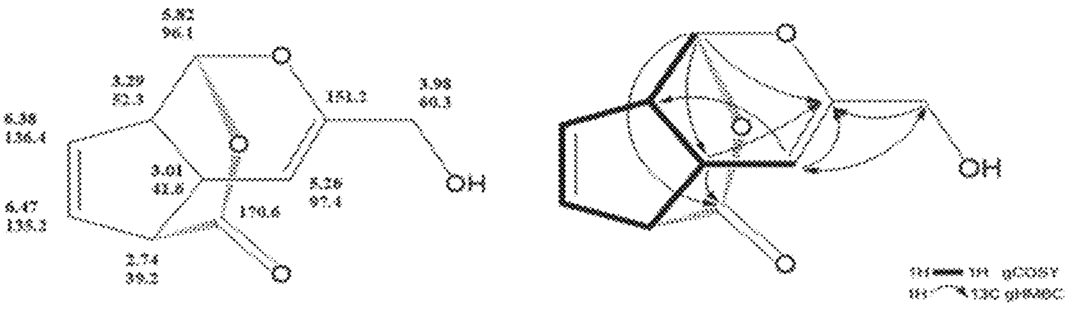

【Fig 5】
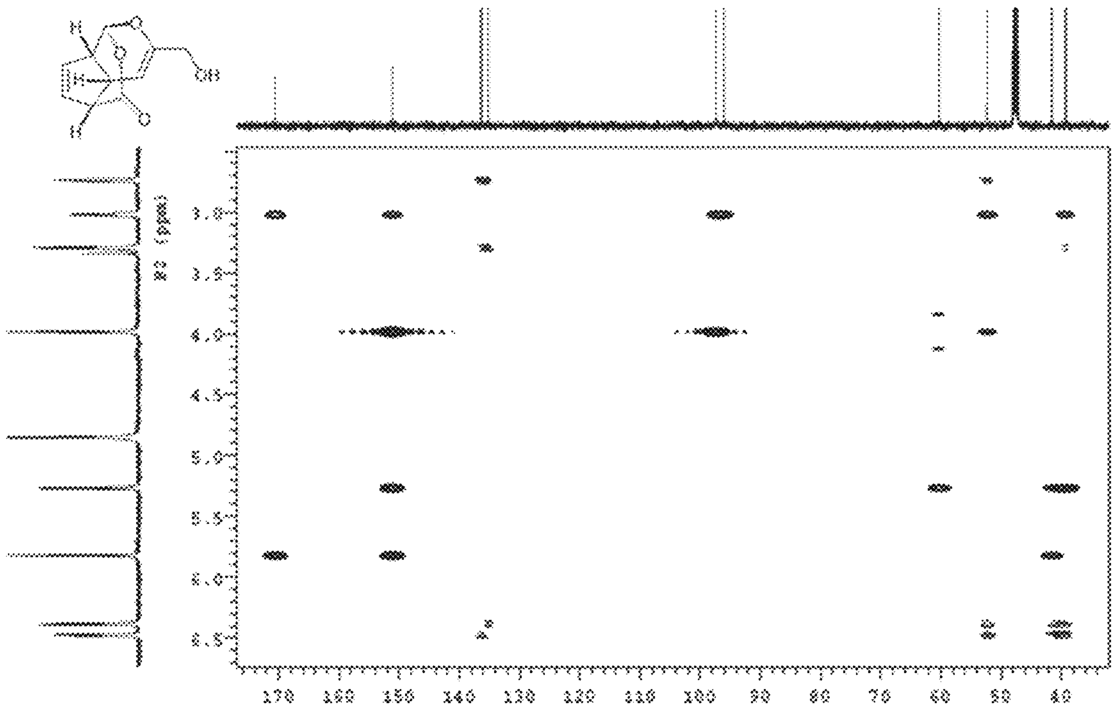
【Fig 6】
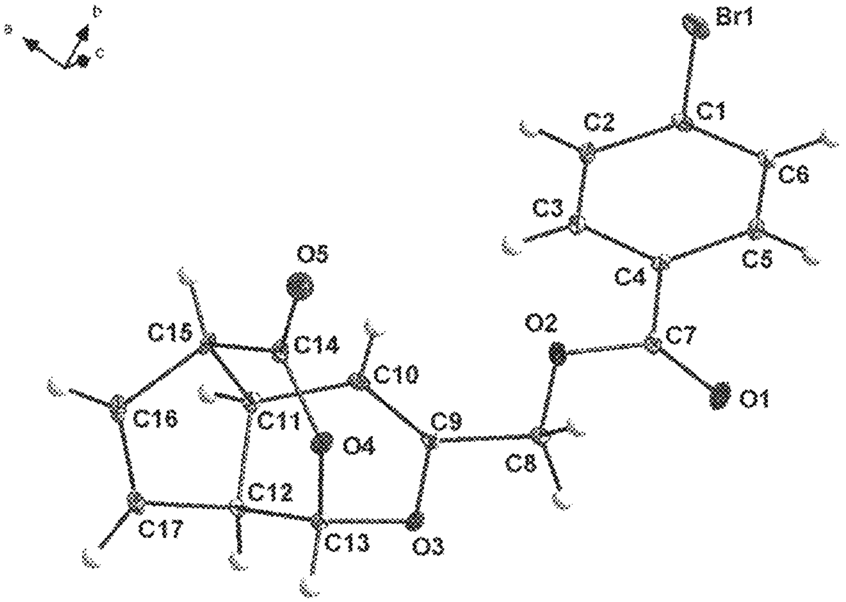

【Fig 7】
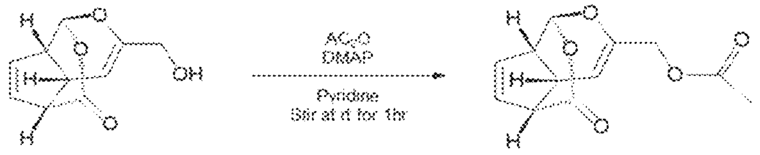
1 2
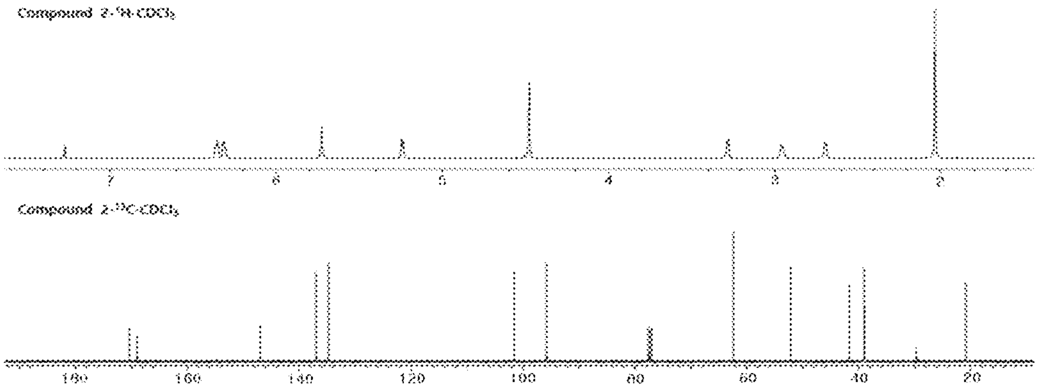
【Fig 8】
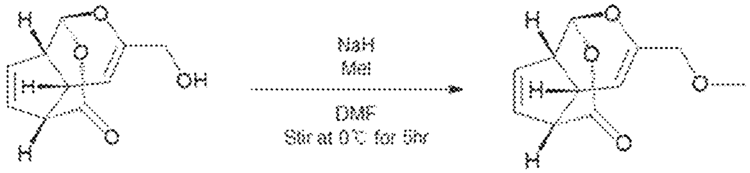
1 3
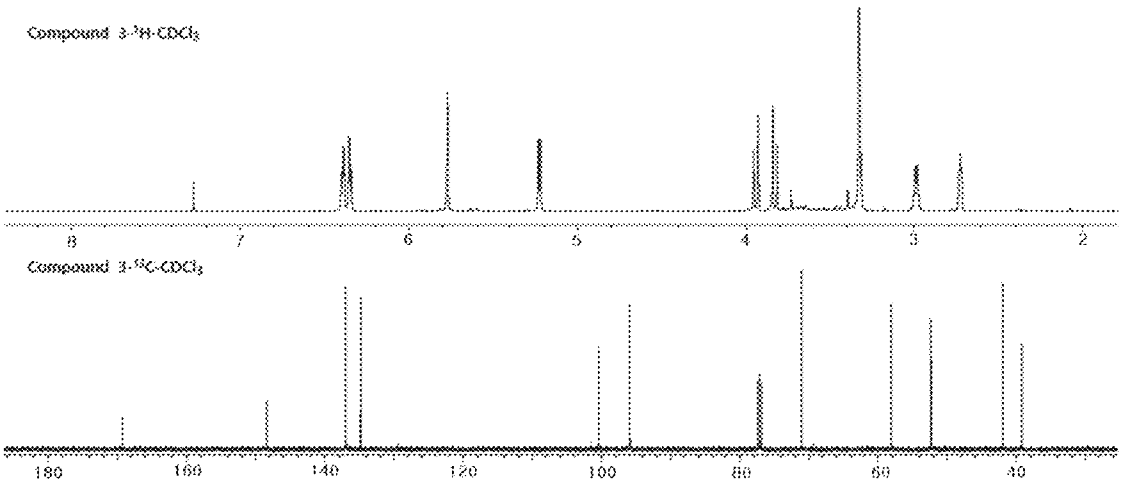

【Fig 9】
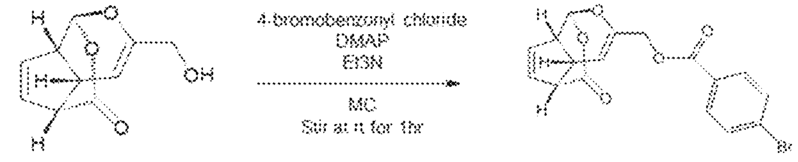
1
4
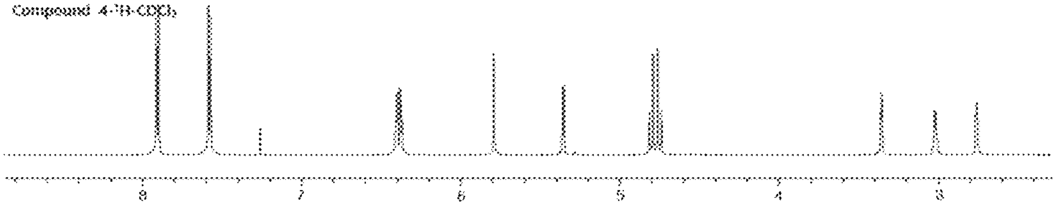
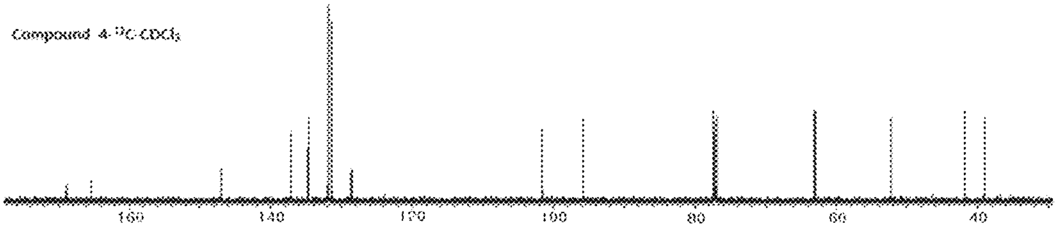
【Fig 10】
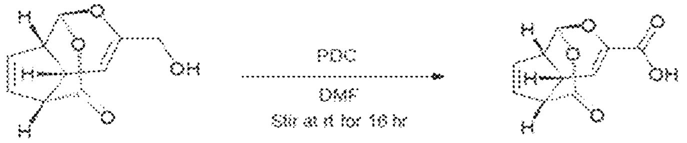
1
5
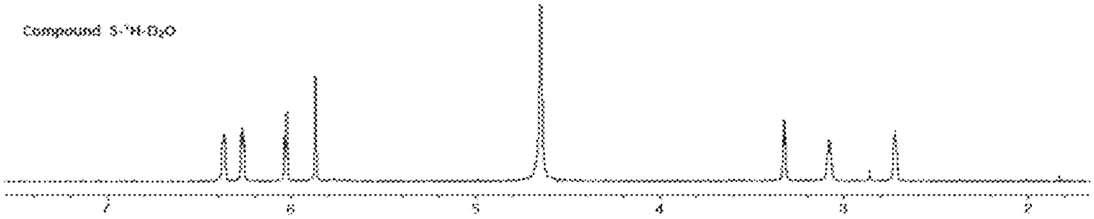
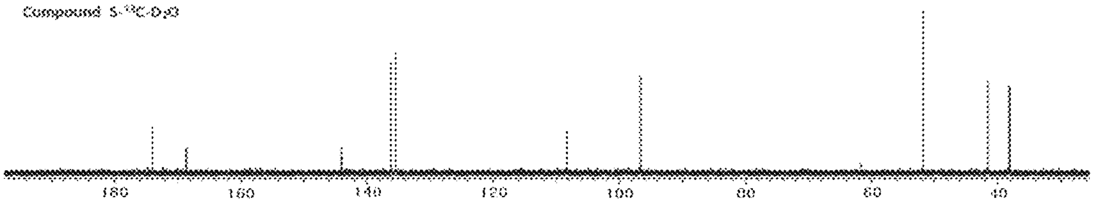

【Fig 11】
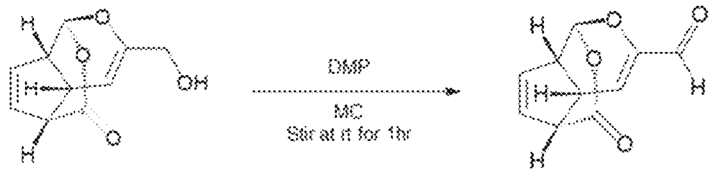
1
6
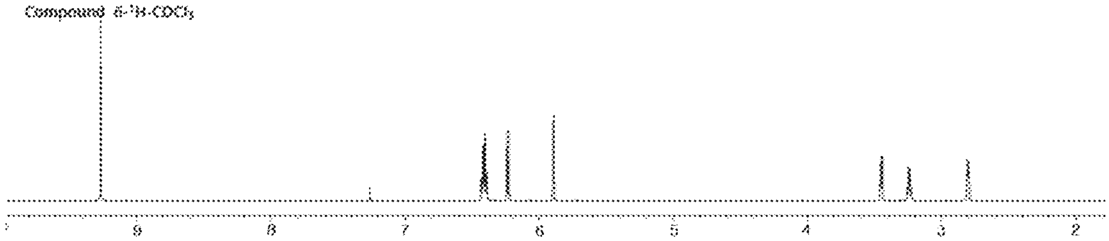
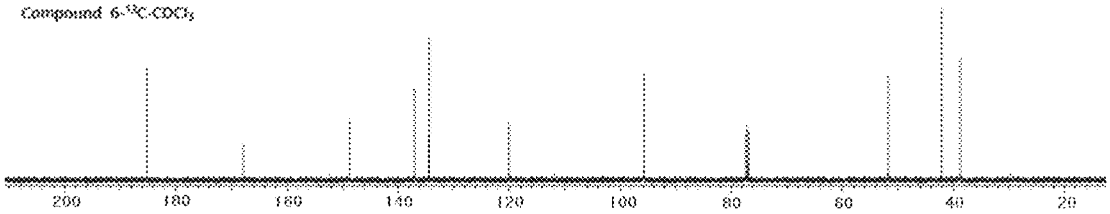
【Fig 12】
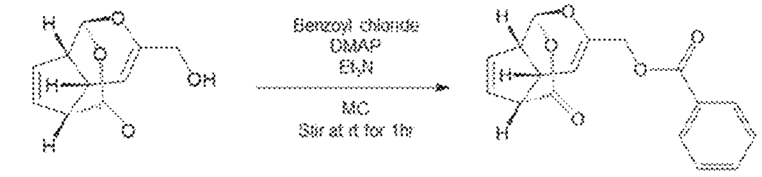
1
7
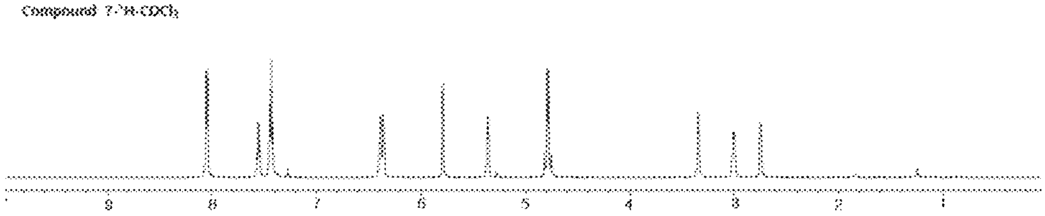
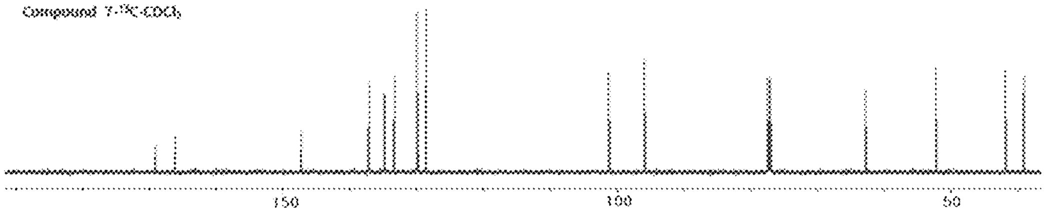

【Fig 13】
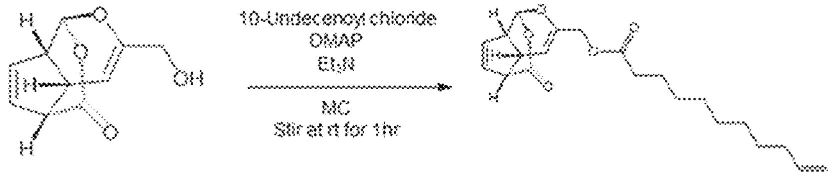
1
8
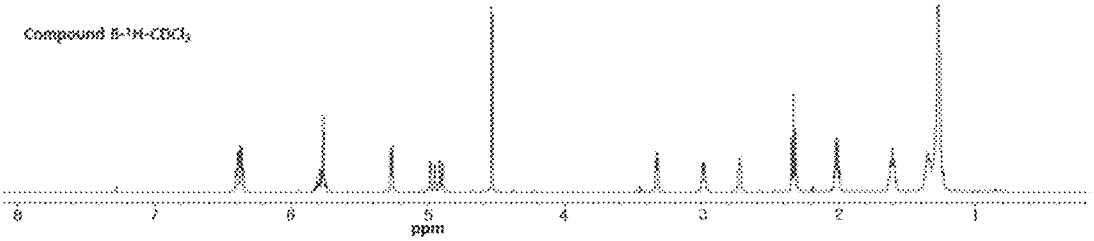
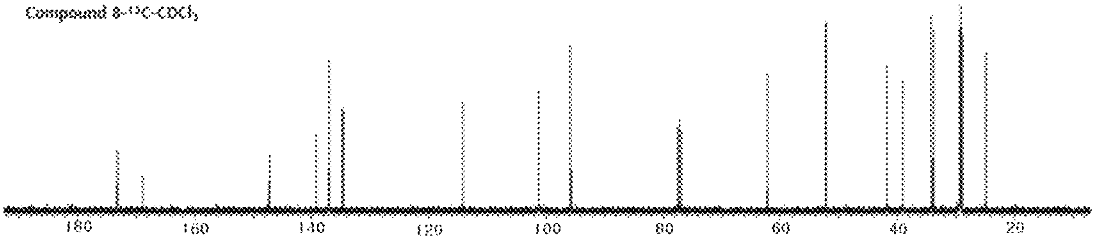
【Fig 14】
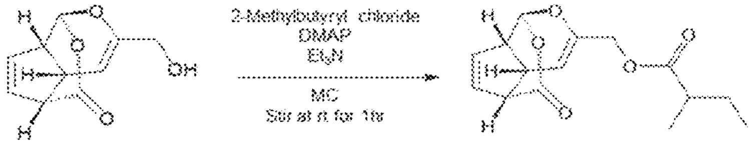
1
9
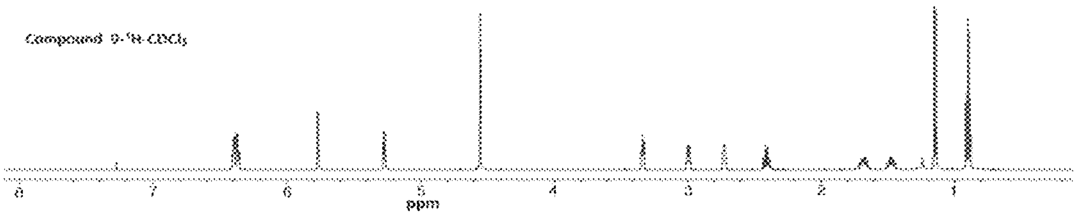
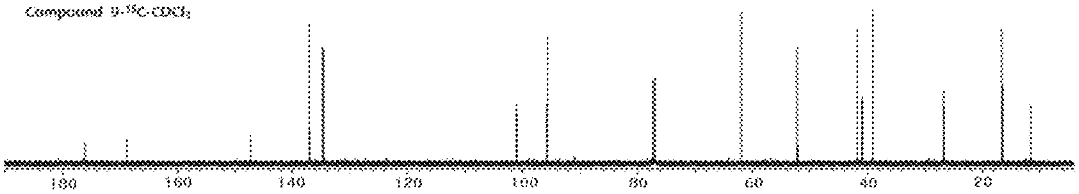

【Fig 15】
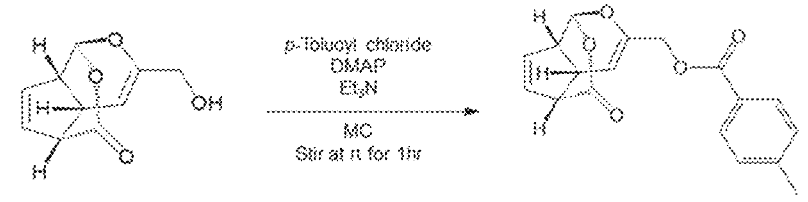
1 10
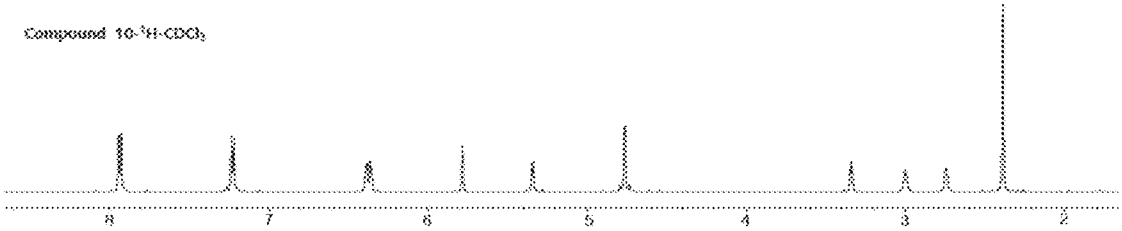
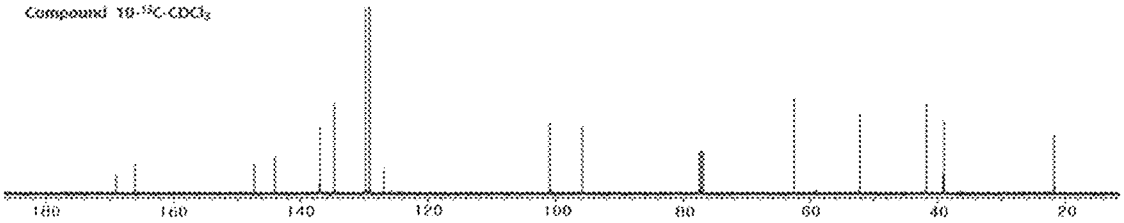
【Fig 16】
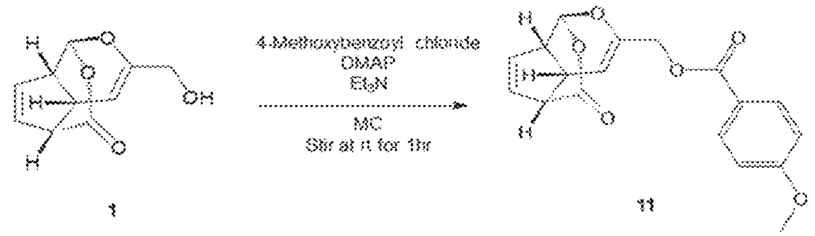
1 11
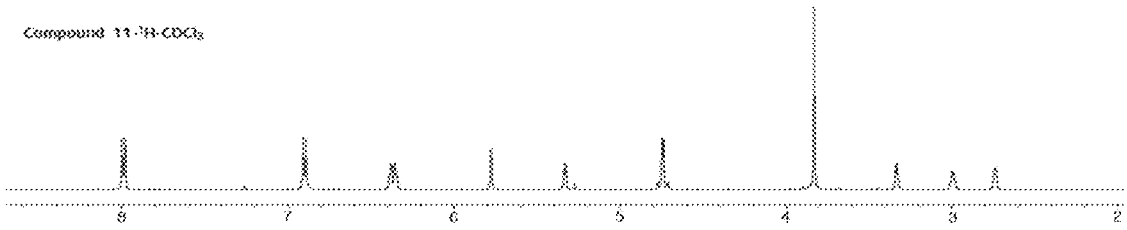
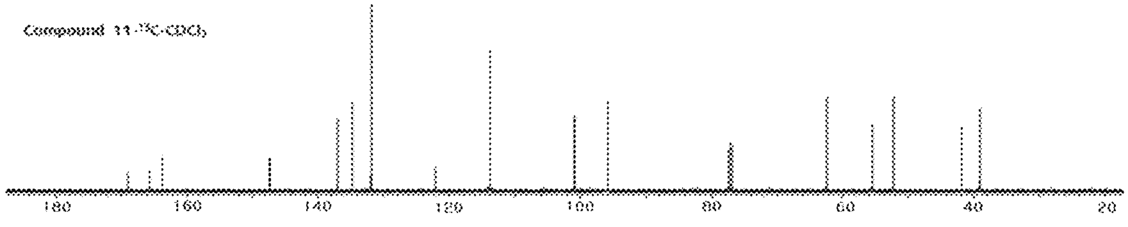

【Fig 17】
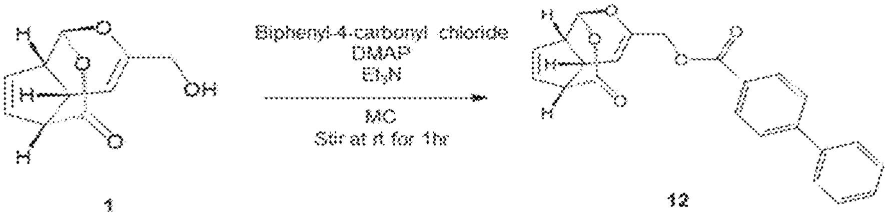
1 12
Compound 12-1H-CDCl3
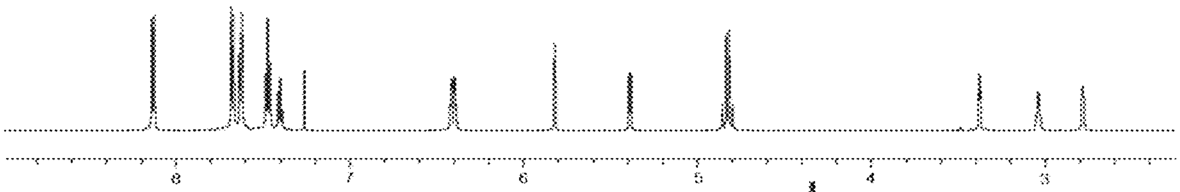
Compound 12-13C-CDCl3
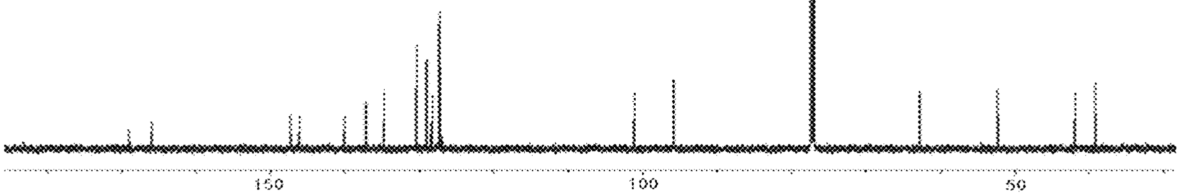
【Fig 18】
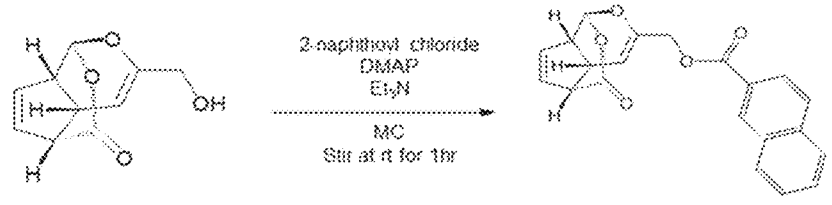
1 13
Compound 13-1H-CDCl3
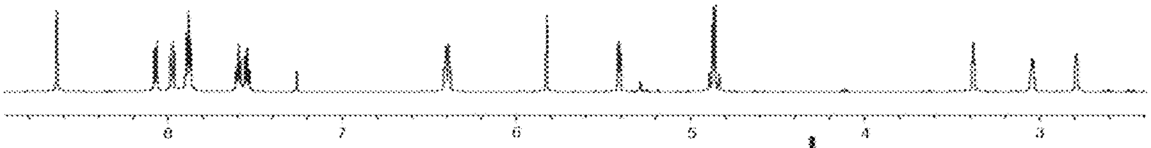
Compound 13-13C-CDCl3
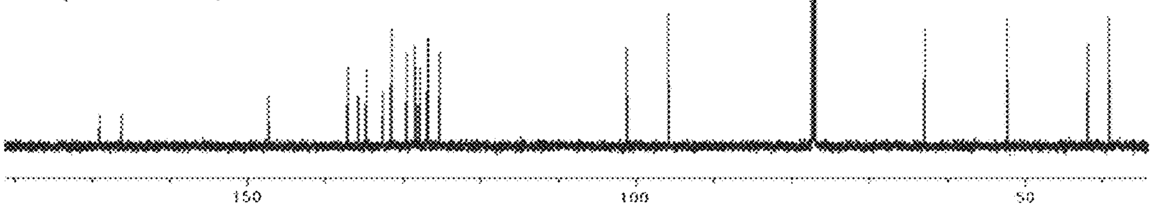

【Fig 19】
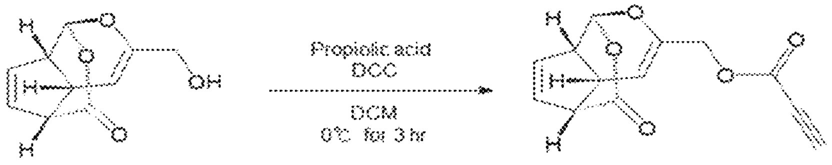
1 14
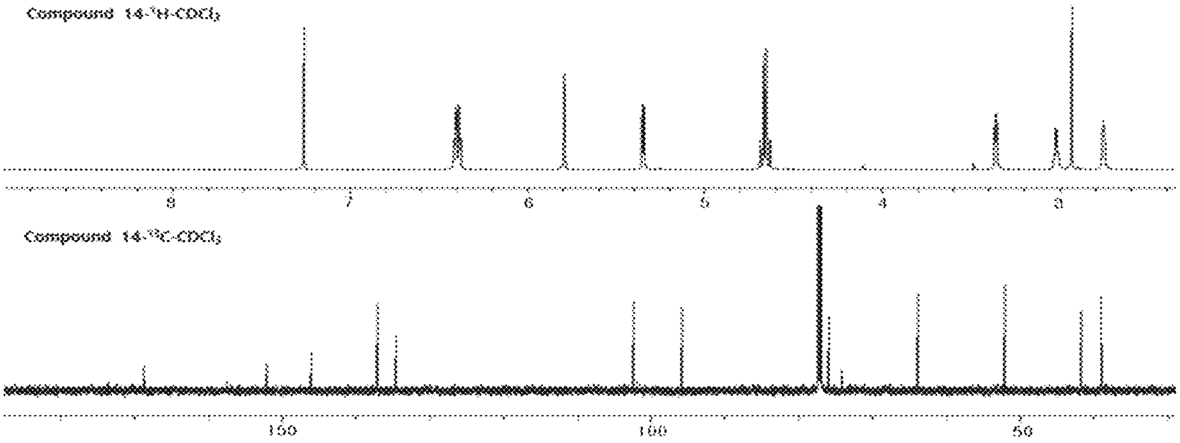
【Fig 20】
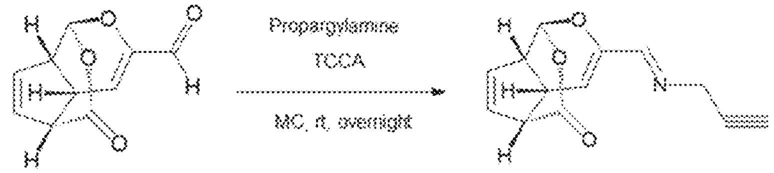
6 15
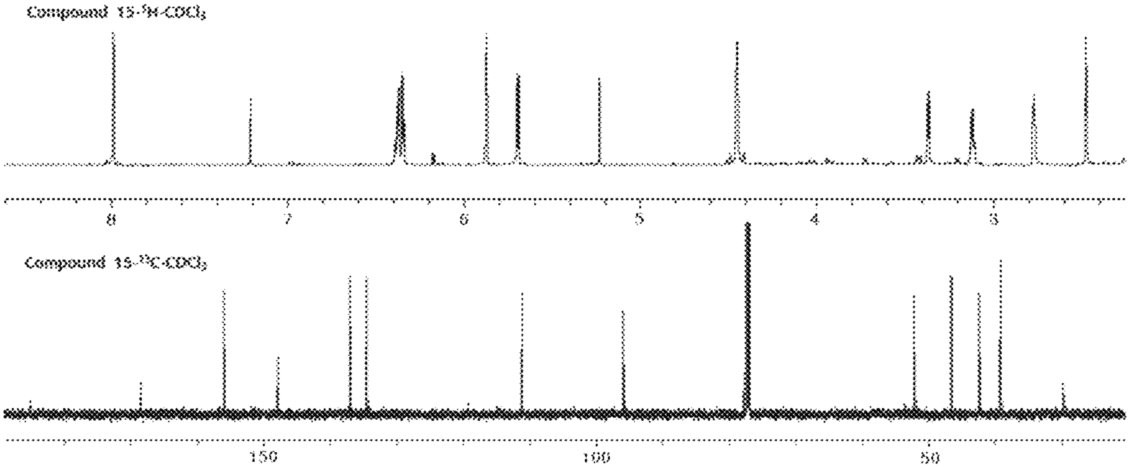

【Fig 21】
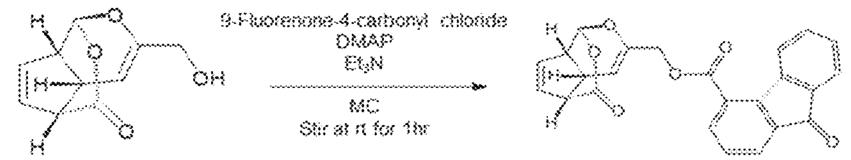
1
16
Compound 16-$^{1}$H-$CDCl_3$
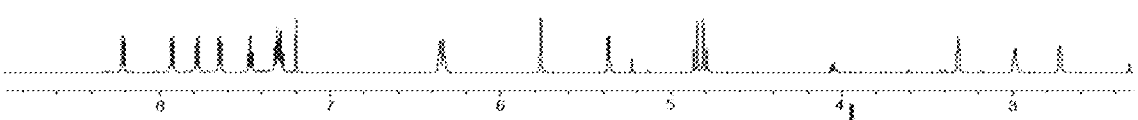
Compound 16-$^{13}$C-$CDCl_3$
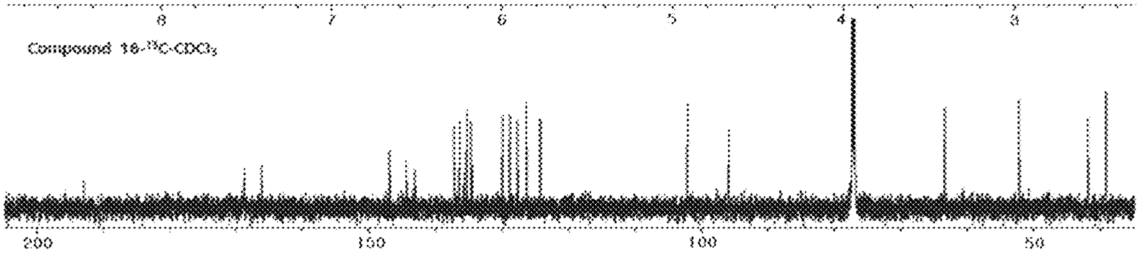
【Fig 22】
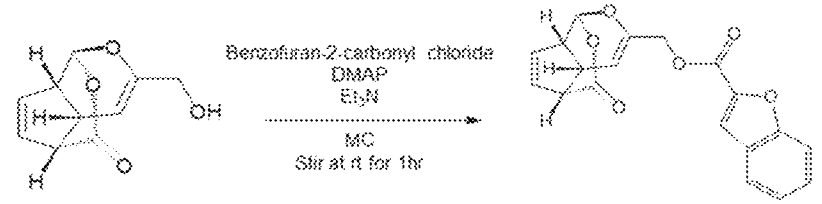
1
17
Compound 17-$^{1}$H-$CDCl_3$
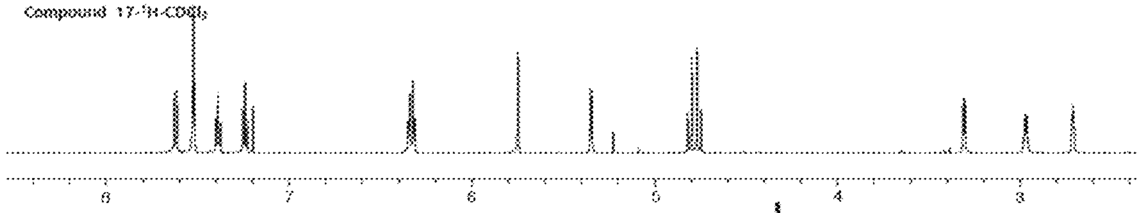
Compound 17-$^{13}$C-$CDCl_3$
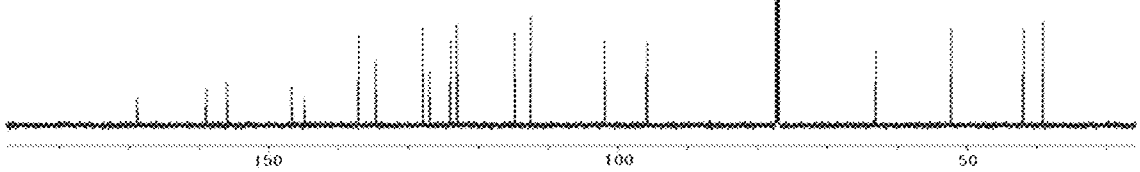

【Fig 23】
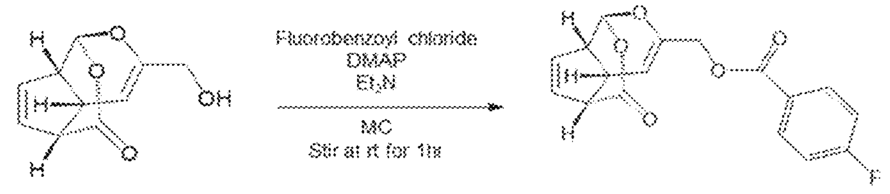
1 18
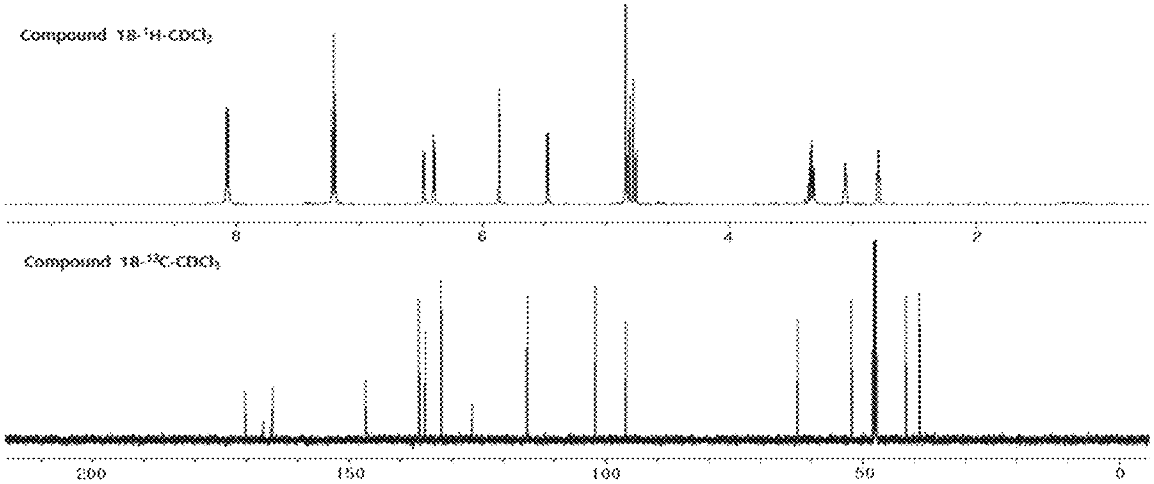
【Fig 24】
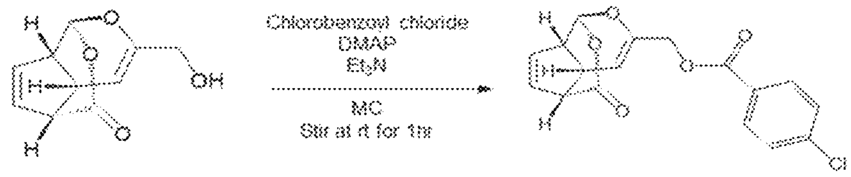
1 19
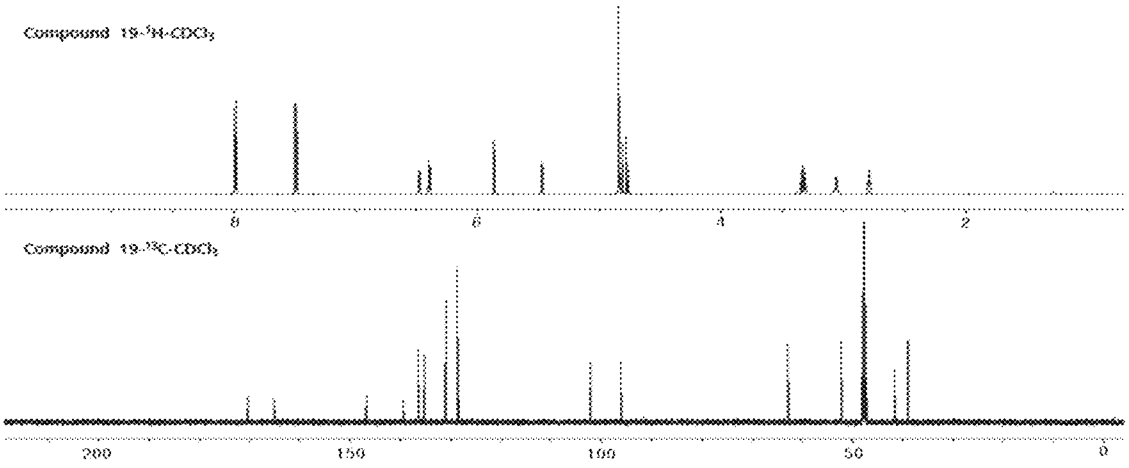

【Fig 25】
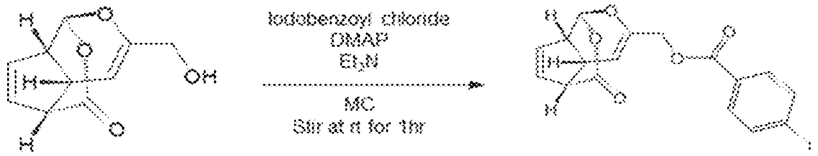
1 20
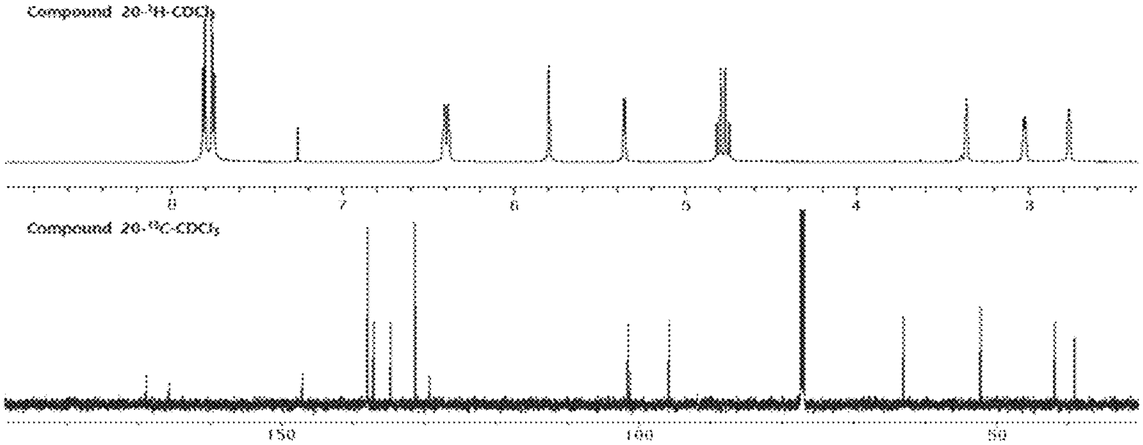
【Fig 26】
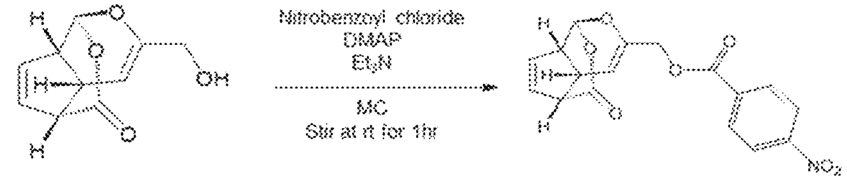
1 21
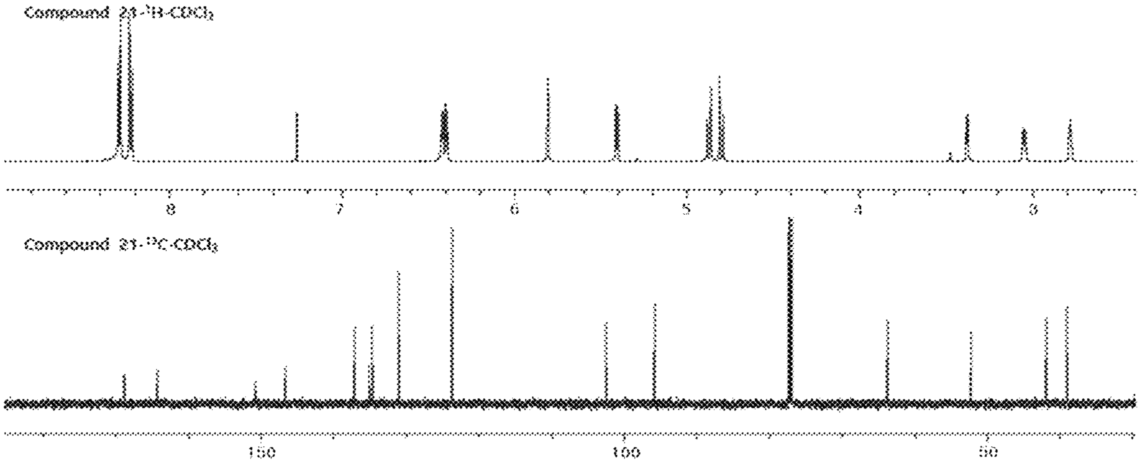

【Fig 27】
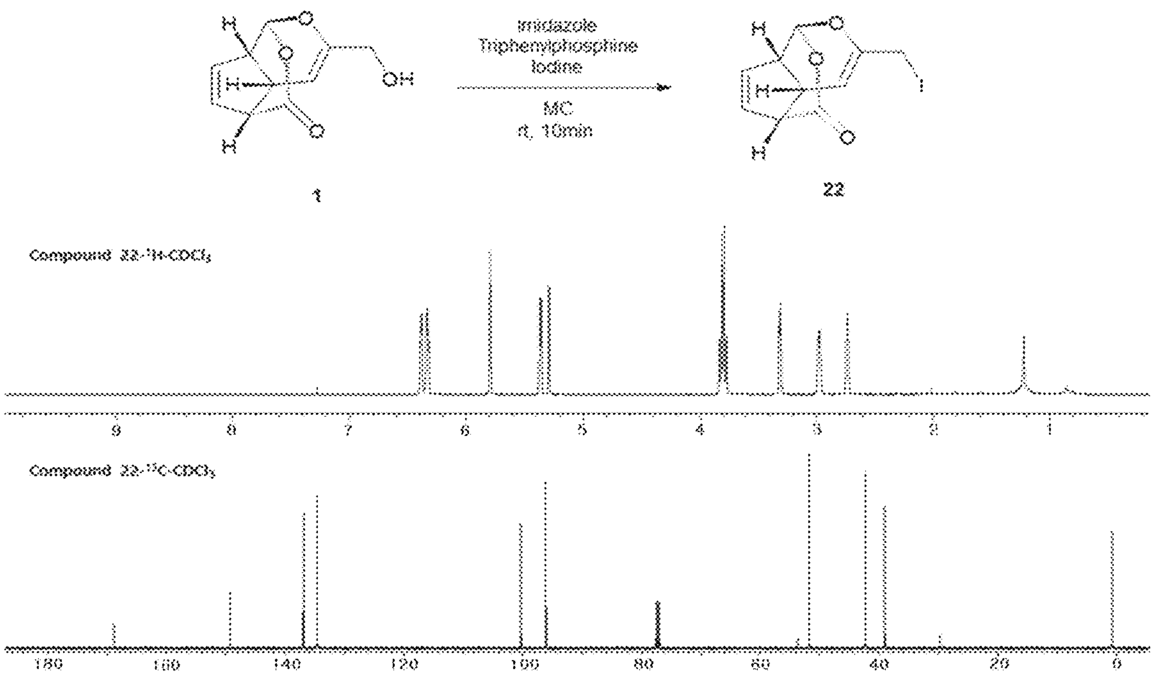
【Fig 28】
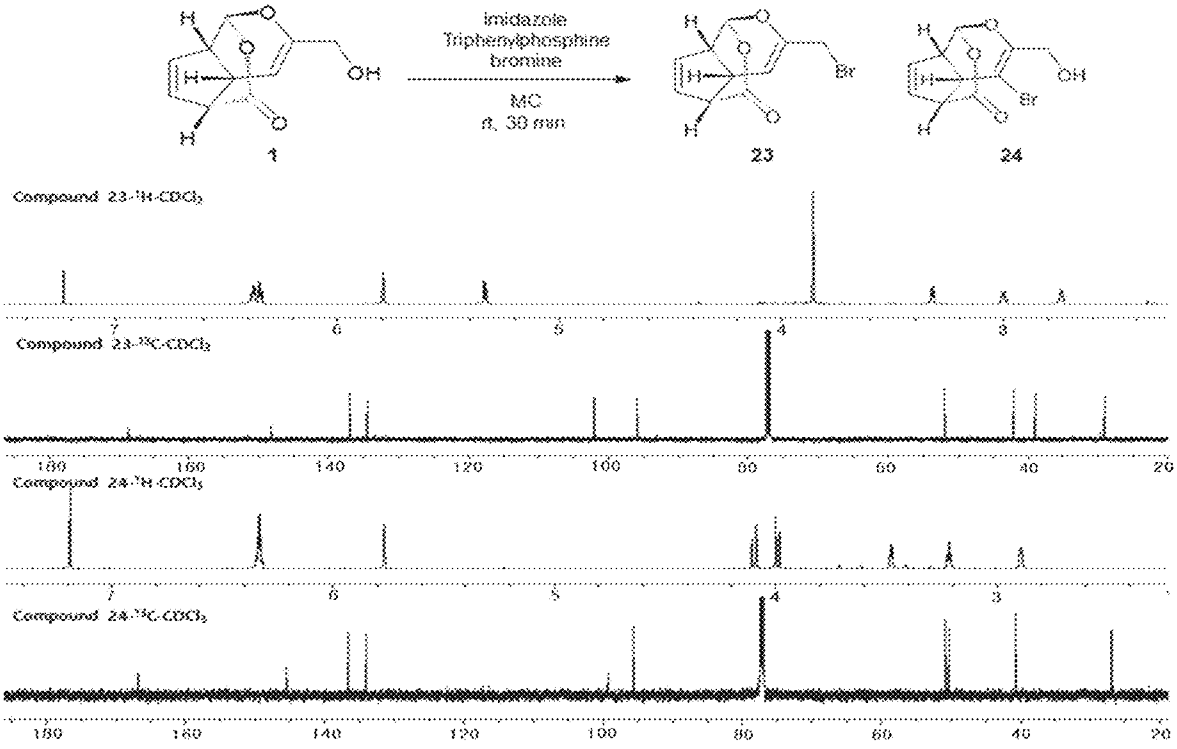

【Fig 29】
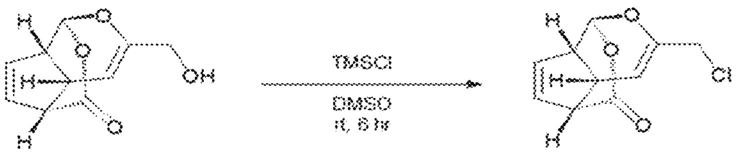
1
25
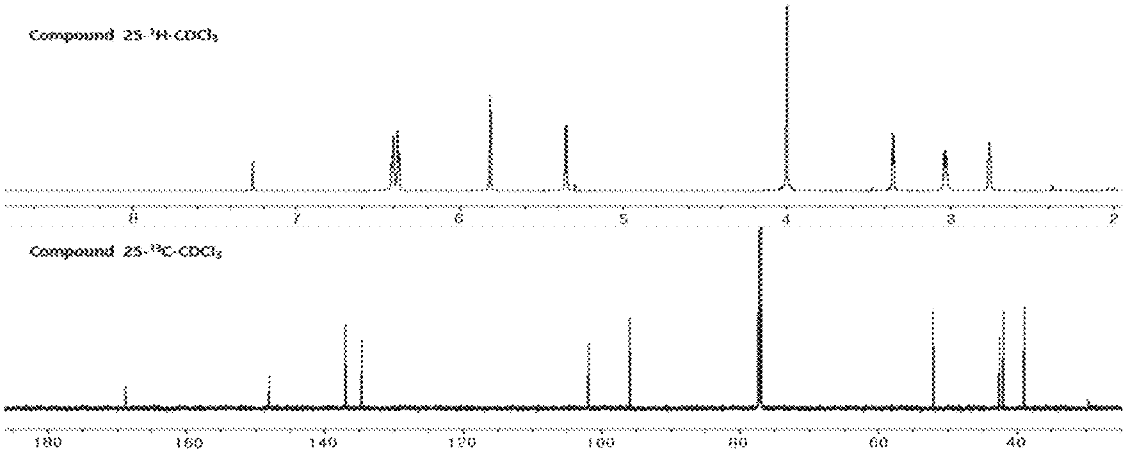
【Fig 30】
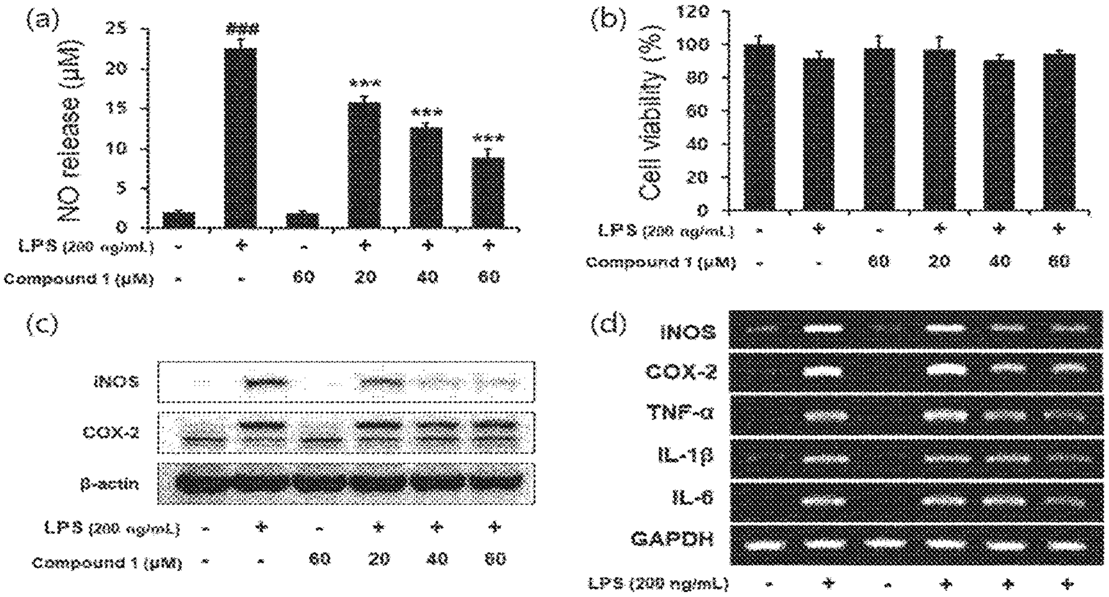

【Fig 31】
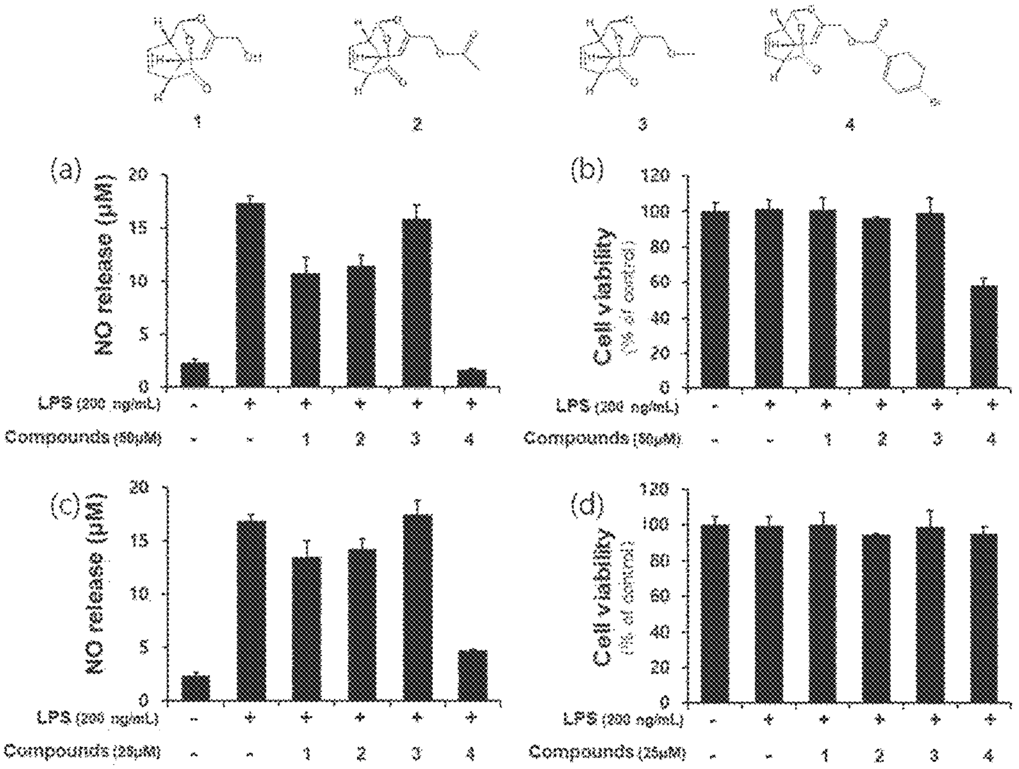

【Fig 32】
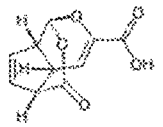
5
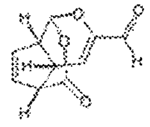
6
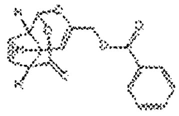
7
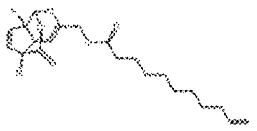
8
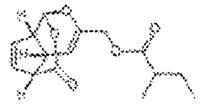
9
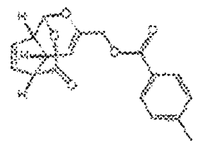
10
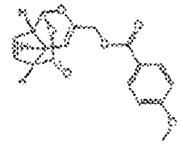
11
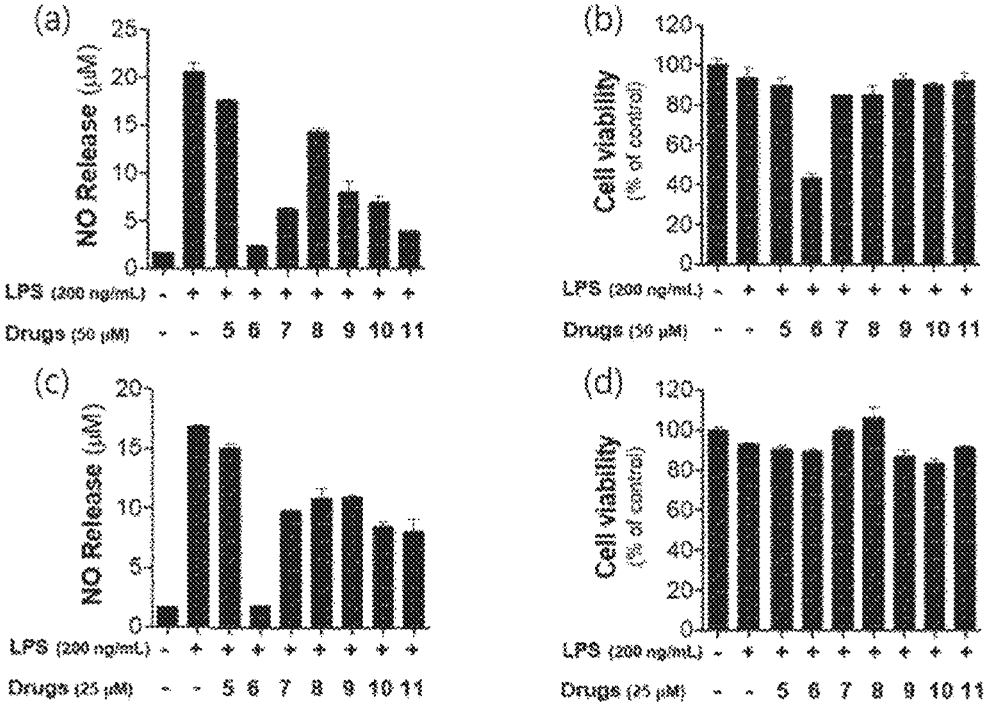

【Fig 33】
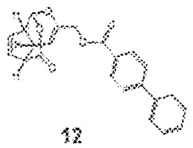
12
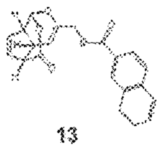
13
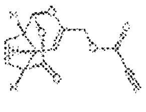
14
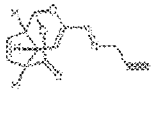
15
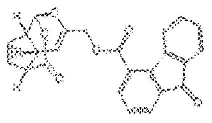
16
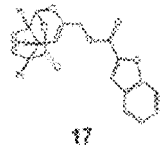
17
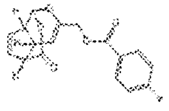
18
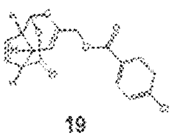
19
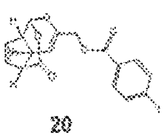
20
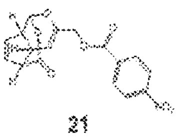
21
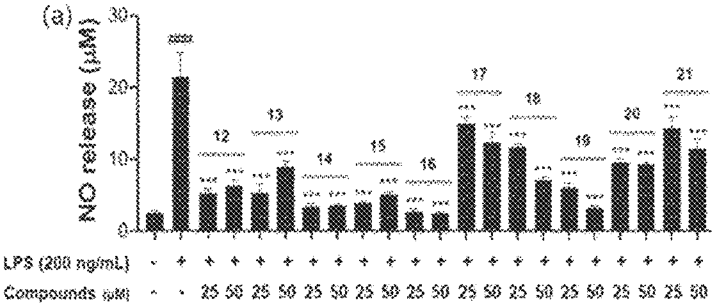
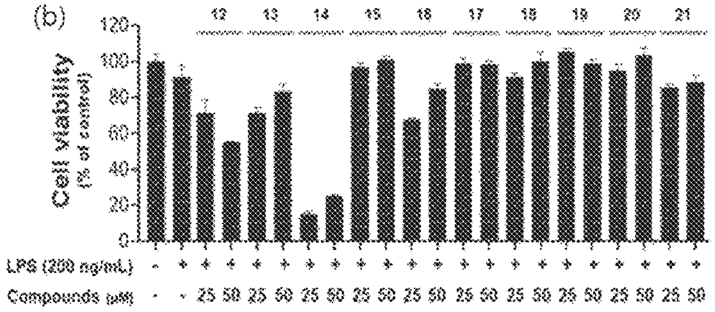

【Fig 34】
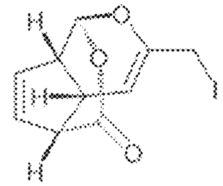
22
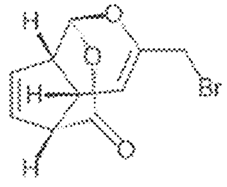
23
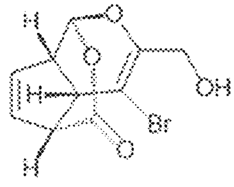
24
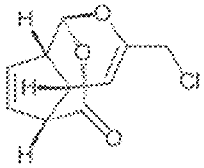
25
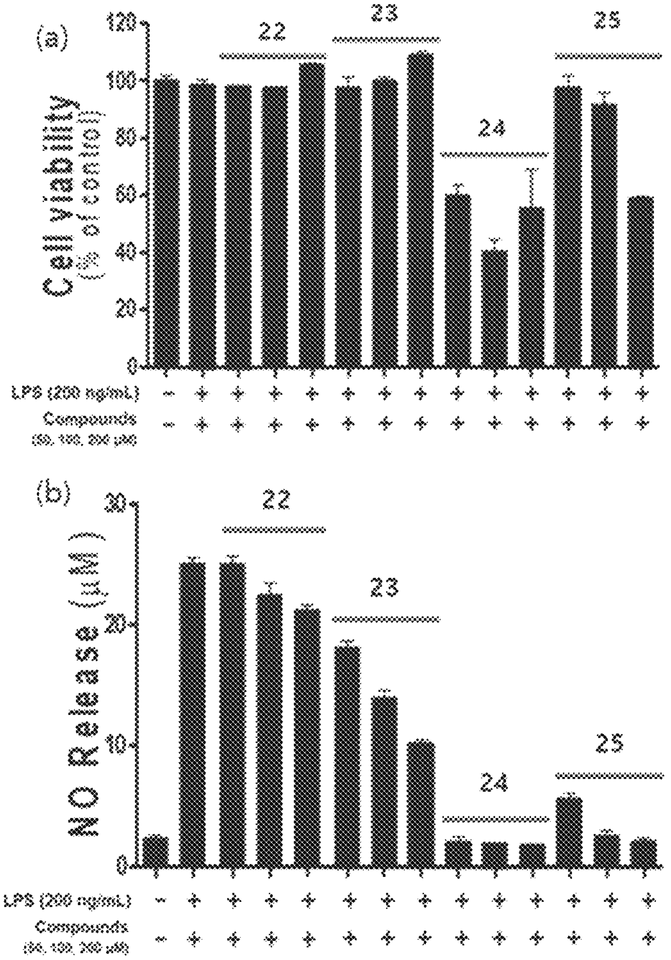

【Fig 35】
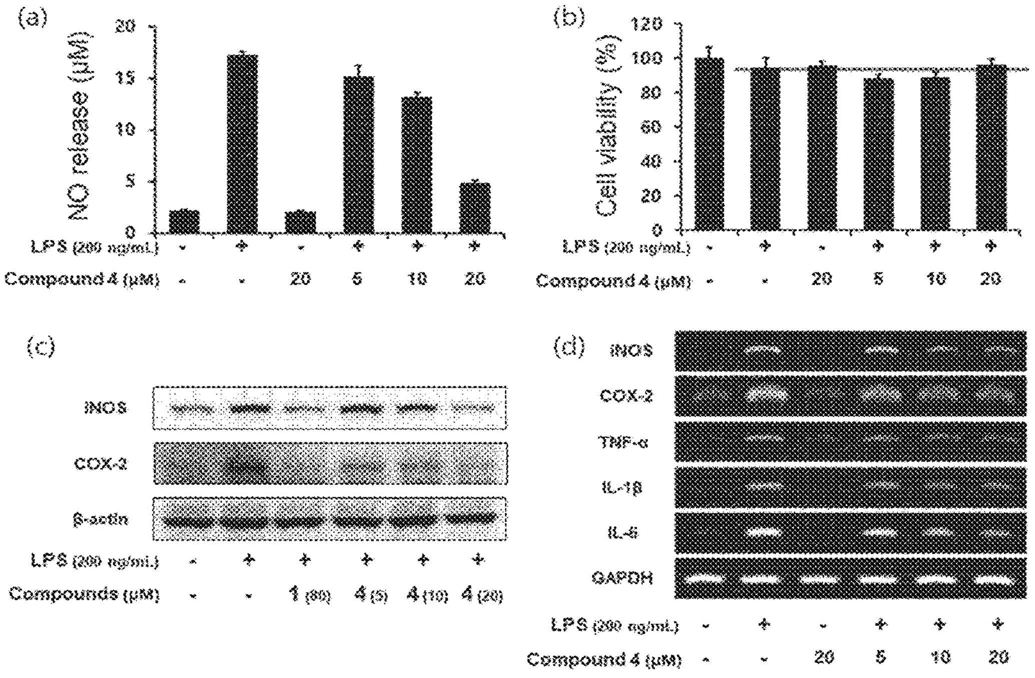
【Fig 36】
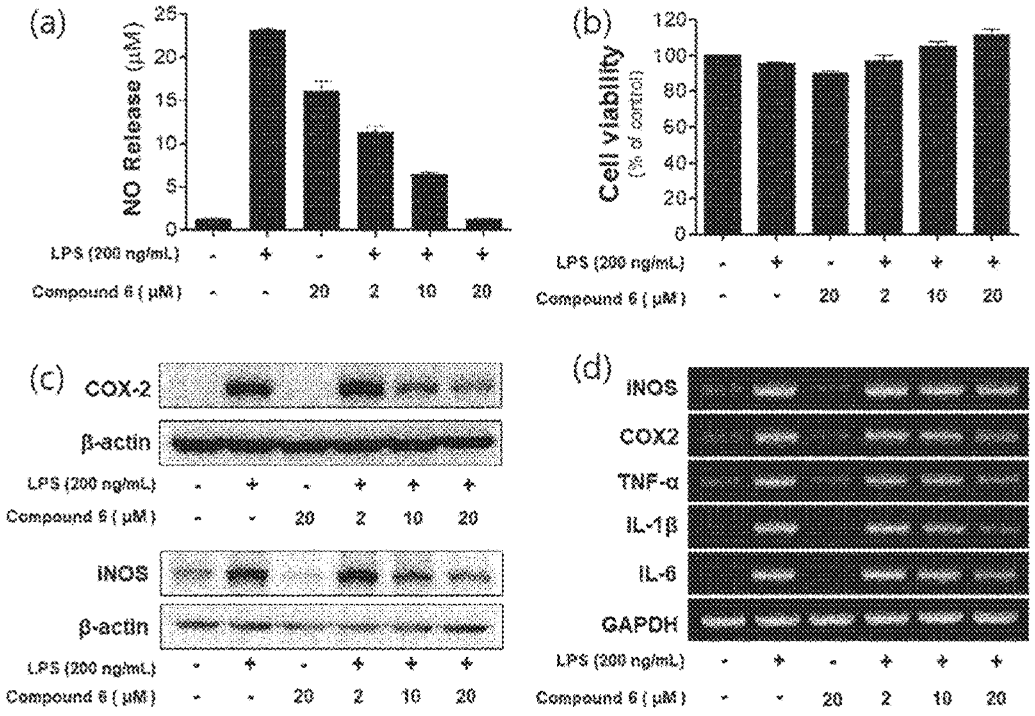

【Fig 37】
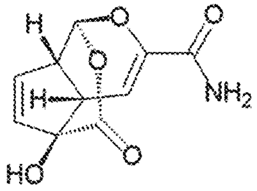
26
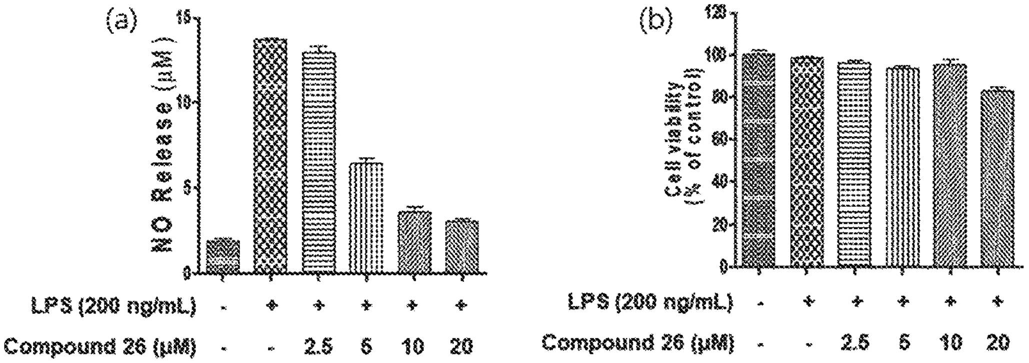

COMPOUND AND COMPOSITION FOR PREVENTING OR TREATING NEUROINFLAMMATORY BRAIN DISEASES COMPRISING SAME AS ACTIVE INGREDIENT

TECHNICAL FIELD

The present invention relates to a novel compound and a composition for preventing or treating neuroinflammatory brain diseases including the novel compound as an active ingredient.

BACKGROUND ART

The central nervous system consists of nerve cells and glial cells. The glial cells account for about 90% of all brain cells and about 50% by volume of the entire brain. The glial cells may be further classified into three types: astrocytes, microglia, and oligodendrocytes. Among these, the microglia are a type of specialized macrophage and are widely distributed in the brain. The microglia not only function as phagocytes that ingest tissue debris and dead cells, but also participate in the biological defense activities of the brain.

Neuroinflammation is a type of immune response in the nervous system and is closely related to many neurodegenerative diseases, including Alzheimer's disease, Parkinson's disease, and multiple sclerosis, and has been currently considered as a typical feature of neurodegenerative diseases. Neuroinflammatory responses include activation of innate immune cells (microglia), release of inflammatory mediators such as nitric oxide (NO), cytokines and chemokines, and macrophage infiltration, which leads to neuronal cell death. Inflammatory activation of microglia and astrocytes is considered as a pathological marker and an important mechanism in the progression of neurodegenerative diseases. Strict regulation of the microglial activity is essential for maintaining brain homeostasis and preventing infectious and inflammatory diseases.

Although many studies have been attempted to treat neuroinflammatory diseases, no commercially available substances have yet been developed that have clearly proven their effectiveness so as to be applied to a wide range of neuroinflammatory diseases, research on a new therapeutic agent is required.

Under the background, there was a need to develop a therapeutic agent that was safer and had an excellent neuroprotective effect. Therefore, the present inventors confirmed that compounds extracted from strains collected from the Kosrae Island and semi-synthetic derivatives using the compounds were effective in preventing or treating neuroinflammatory brain diseases, and then completed the present invention. In addition, the present inventors confirmed that (1S,4aS,5R,7aS)-8-oxo-1,4a,5,7a-tetrahydro-1,5-(epoxymethano)cyclopenta[c]pyran-3-carboxamide was effective in preventing or treating neuroinflammatory brain diseases, and then completed the present invention.

DISCLOSURE

Technical Problem

The present invention has been made in an effort to provide a novel compound, an isomer thereof, or a pharmaceutically acceptable salt thereof.

The present invention has also been made in an effort to provide a use of the novel compound, an isomer thereof, or a pharmaceutically acceptable salt thereof.

The present invention has also been made in an effort to provide a use of (1S,4aS,5R,7aS)-8-oxo-1,4a,5,7a-tetrahydro-1,5-(epoxymethano)cyclopenta[c]pyran-3-carboxamide, an isomer thereof, or a pharmaceutically acceptable salt thereof.

The present invention has also been made in an effort to provide a method for preventing or treating neuroinflammatory brain diseases including administering a compound represented by Chemical Formula 1 below, an isomer or a pharmaceutically acceptable salt thereof to a subject in need thereof.

[Chemical Formula 1]

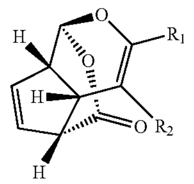

In Chemical Formula 1 above, $R_1$ is —C(=O)$R_a$, —$CH_2R_b$ or —CH=$NCH_2C$≡CH, $R_a$ is any one selected from the group consisting of —H, —OH, —$OCH_3$, —$OCH_2CH_3$, and —$OCH_2CH_2CH_3$, $R_b$ is —$OR_{b1}$ or halogen, $R_{b1}$ is any one selected from the group consisting of —H, —$CH_3$, —$CH_2CH_3$, —$CH_2CH_2CH_3$, —C(=O)$R_{b11}$,

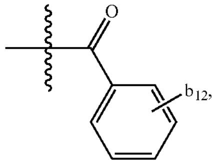
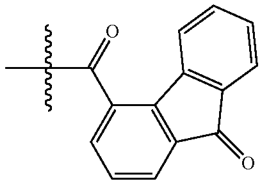
,
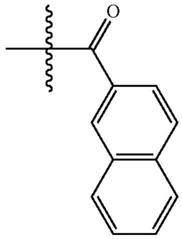
and
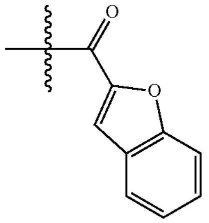
, $R_{b11}$ is a straight-chain or branched-chain $C_1$-$C_5$ alkyl group or a straight-chain or branched-chain $C_6$-$C_{12}$ alkenyl group containing at least one double or triple bond between carbons, $R_{b12}$ is any one selected from the group consisting of —H, —$CH_3$, —$CH_2CH_3$, —$CH_2CH_2CH_3$, halogen, —$OCH_3$ and —$OCH_2CH_3$, —$NO_2$ and a phenyl group, and $R_2$ is —H or halogen.

The present invention has also been made in an effort to provide a method for preventing or treating neuroinflammatory brain diseases including administering a compound represented by Chemical Formula 2 below, an isomer or a pharmaceutically acceptable salt thereof to a subject in need thereof.

[Chemical Formula 2]

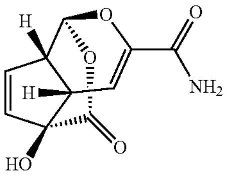

Technical Solution

Compound of Chemical Formula 1

An aspect of the present invention provides a compound represented by Chemical Formula 1 below, an isomer thereof or a pharmaceutically acceptable salt thereof:

[Chemical Formula 1]

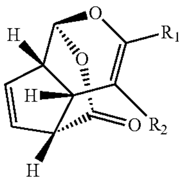

In Chemical Formula 1 above, $R_1$ is —C(═O)$R_a$, —$CH_2R_b$ or —CH═$NCH_2C$≡CH, $R_a$ is any one selected from the group consisting of —H, —OH, —$OCH_3$, —$OCH_2CH_3$, and —$OCH_2CH_2CH_3$, $R_b$ is —$OR_{b1}$ or halogen, $R_{b1}$ is any one selected from the group consisting of —H, a straight-chain or branched-chain $C_1$-$C_5$ alkyl, —C(═O)$R_{b11}$,

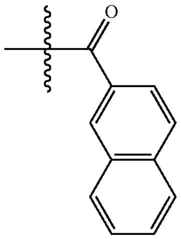

and

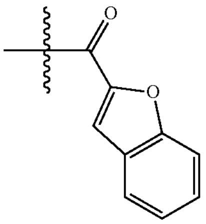

, $R_{b11}$ is a $C_1$-$C_5$ alkyl group or a straight-chain or branched-chain $C_6$-$C_{12}$ alkenyl group containing at least one double or triple bond between carbons, $R_{b12}$ is any one selected from the group consisting of —H, —$CH_3$, —$CH_2CH_3$, —$CH_2CH_2CH_3$, halogen, —$OCH_3$, —$OCH_2CH_3$, —$NO_2$ and a phenyl group, and $R_2$ may be —H or halogen.

In an embodiment, in the compound represented by Chemical Formula 1, $R_1$ may be —C(═O)$R_a$ and $R_a$ may be —H or —OH.

In another embodiment, in the compound represented by Chemical Formula 1, $R_1$ may be —$CH_2R_b$, $R_b$ may be —$OR_{b1}$ or halogen, $R_{b1}$ may be any one selected from the group consisting of —H, straight-chain or branched-chain $C_1$-$C_5$ alkyl, —C(═O)$R_{b11}$,

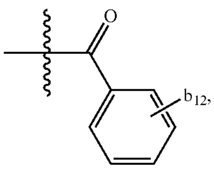

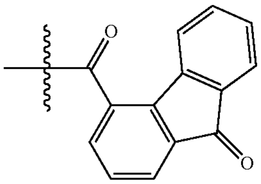

,

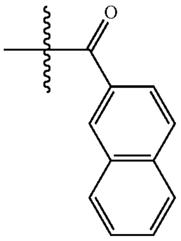

and

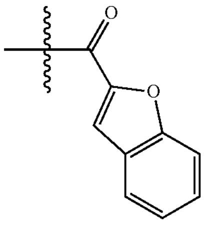

, $R_{b11}$ may be a straight-chain or branched-chain $C_1$-$C_5$ alkyl group or straight-chain or branched-chain $C_6$ to $C_{12}$ alkenyl group including one or more double or triple bonds between carbons, $R_{b12}$ may be any one selected from the group consisting of —H, —$CH_3$, —$CH_2CH_3$, —$CH_2CH_2CH_3$, halogen, —$OCH_3$ and —$OCH_2CH_3$, —$NO_2$ and a phenyl group, and $R_2$ may be —H or halogen.

In another embodiment, in the compound represented by Chemical Formula 1, $R_{b1}$ may be any one selected from the group consisting of —H, -straight-chain or branched-chain $C_1$-$C_3$ alkyl, —C(═O)$R_{b11}$.

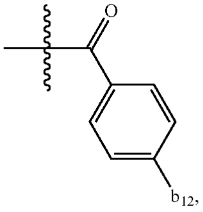

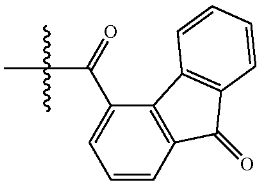

,

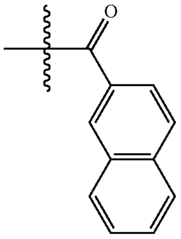

and

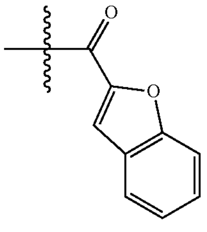

.

In another embodiment, in the compound represented by Chemical Formula 1, $R_{b11}$ may be any one selected from the group consisting of —$CH_3$,

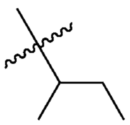

,

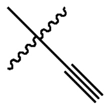

, and

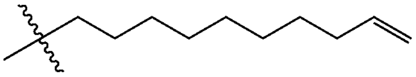

.

The compound represented by Chemical Formula 1 of the present invention may contain one or more stereocenters and thus may exist as respective optical isomers.

Further, according to an embodiment of the present invention, the compound of Chemical Formula 1 may be any one selected from the group consisting of the following compounds:

| Example | Structure | IUPAC name |
|---|---|---|
| Compound 1 | 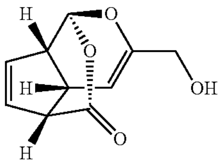 | (1S,4aS,5R,7aS)-3-(hydroxymethyl)-1,4a,5,7a-tetrahydro-1,5 (epoxymethano) cyclopenta[c]pyran-8-one |
| Compound 2 | 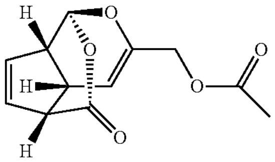 | ((1S,4aS,5R,7aS)-8-oxo-1,4a,5,7a-tetrahydro-1,5-(epoxymethano)cyclopenta[c] pyran-3-y])methyl acetate |
| Compound 3 | 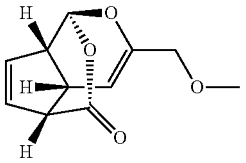 | (1S,4aS,5R,7aS)-3-(methoxymethyl)-1,4a,5,7a-tetrahydro-1,5-(epoxymethano)cyclopenta[c]pyran-8-one |
| Compound 4 | 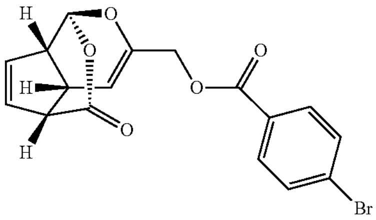 | ((1S,4aS,5R,7aS)-8-oxo-1,4a,5,7a-tetra hydro-1,5-(epoxymethano)cyclopesta[c] pyran-3-yl)methyl 4-bromobenzoate |
| Compound 5 | 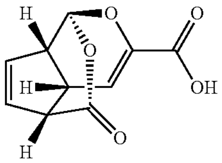 | (1S,4aS,5R,7aS)-8-oxo-1,4a,5,7a-tetrahydro-1,5-(epoxymethano)cyclopenta[c] pyran-3-carboxylic acid |
| Compound 6 | 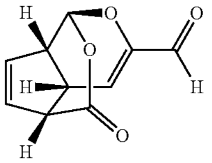 [SMILES: O=CC1=C[C@H]2[C@@H]3C=C[C@H]2C(=O)O[C@@H]3O1] | (1S,4aS,5R,7aS)-8-oxo-1,4a,5,7a-tetrahydro-1,5-(epoxymethano)cyclopenta[c] pyran-3-carbaldehyde |
| Compound 7 | 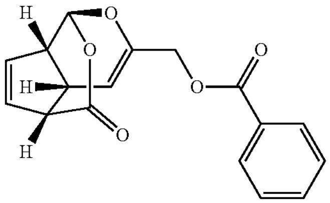 [SMILES: O=C(OCC1=C[C@H]2[C@@H]3C=C[C@H]2C(=O)O[C@@H]3O1)c1ccccc1] | ((1S,4aS,5R,7aS)-8-oxo-1,4a,5,7a-tetrahydro-1,5-(epoxymethano)cyclopenta[c] pyran-3-yl)methyl benzoate |

-continued

| Example | Structure | IUPAC name |
|---|---|---|
| Compound 8 | 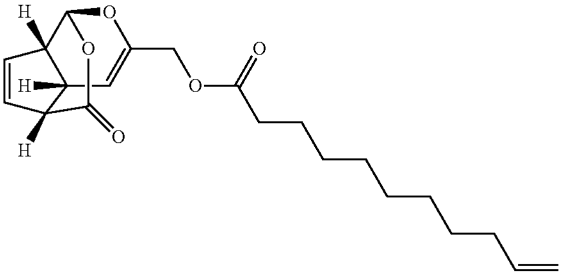 [SMILES: C=CCCCCCCCCC(=O)OCC1=C[C@H]2[C@@H]3C=C[C@H]2C(=O)O[C@@H]3O1] | ((1S,4aS,5R,7aS)-8-oxo-1,4a,5,7a-tetra-hydro-1,5-(epoxymethano)cyclopenta[c] pyran-3-yl)methylundec-10-enoate |
| Compound 9 | 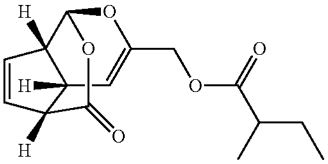 [SMILES: CCC(C)C(=O)OCC1=C[C@H]2[C@@H]3C=C[C@H]2C(=O)O[C@@H]3O1] | ((1S,4a5,5R,7aS)-8-oxo-1,4a,5,7a-tetra-hydro-1,5-(epoxymethano)cyclopenta[c] pyran-3-yl)methyl 2-methyl butanoate |
| Compound 10 | 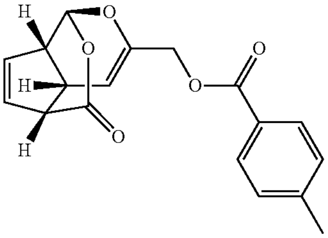 [SMILES: Cc1ccc(C(=O)OCC2=C[C@H]3[C@@H]4C=C[C@H]3C(=O)O[C@@H]4O2)cc1] | (1S,4aS,5R,7aS)-8-oxo-1,4a,5,7a-tetra hydro-1,5-(epoxymethano)cyclopenta[c] pyran-3-yl)methyl 4-methyl benzoate |
| Compound 11 | 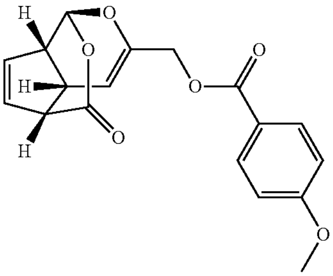 [SMILES: COc1ccc(C(=O)OCC2=C[C@H]3[C@@H]4C=C[C@H]3C(=O)O[C@@H]4O2)cc1] | ((1S,4aS,5R,7aS)-8-oxo-1,4a,5,7a-tetra-hydro-1,5-(epoxymethano)cyclopenta[c] pyran-3-yl)methyl 4-methoxybenzoate |
| Compound 12 | 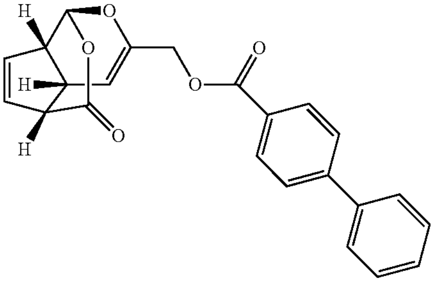 [SMILES: O=C(OCC1=C[C@H]2[C@@H]3C=C[C@H]2C(=O)O[C@@H]3O1)c1ccc(-c2ccccc2)cc1] | ((1S,4aS,5R,7aS)-8-oxo-1,4a,5,7a-tetra-hydro-1,5-(epoxymethano)cyclopenta[c] pyran-3-yl)methyl [1,1'-biphenyl]-4-carboxylate |
| Compound 13 | 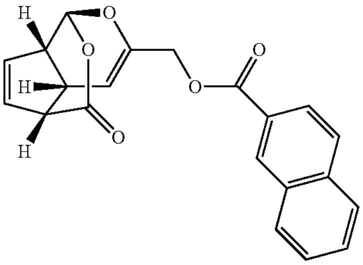 [SMILES: O=C(OCC1=C[C@H]2[C@@H]3C=C[C@H]2C(=O)O[C@@H]3O1)c1ccc2ccccc2c1] | (1S,4aS,5R,7aS) 8-oxo-1,4,5,7a-tetra-hydro-1,5-(epoxymethano)cyclopenta[c] pyran-3-yl)methyl 2-naphthoate |

-continued

| Example | Structure | IUPAC name |
|---|---|---|
| Compound 14 | 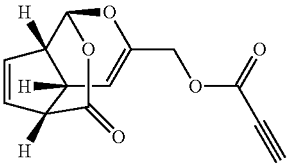 [SMILES: C#CC(=O)OCC1=C[C@H]2[C@@H]3C=C[C@H]2C(=O)O[C@@H]3O1] | ((1S,4aS,5R,7aS)-8-oxo-1,4a,5,7a-tetrahydro-1,5-(epoxymethano)cyclopenta[c]pyran-3-yl)methyl propiolate |
| Compound 15 | 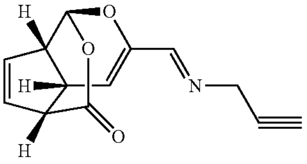 [SMILES: C#CC/N=C/C1=C[C@H]2[C@@H]3C=C[C@H]2C(=O)O[C@@H]3O1] | (1S,4a3,5R,7aS)-3-((E)-(prop-2-yn-1-ylimino)methyl)-1,4a,5,7a-tetrahydro-1,5-(epoxymethano)cyclopenta[c]pyran-8-one |
| Compound 16 | 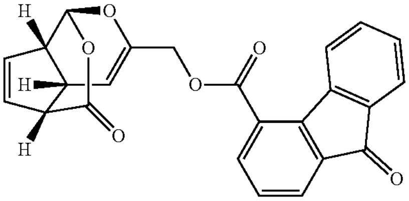 [SMILES: O=C(OCC1=C[C@H]2[C@@H]3C=C[C@H]2C(=O)O[C@@H]3O1)c1cccc2c1-c1ccccc1C2=O] | ((1S,4aS,5R,7aS)-8-oxo-1,4a,5,7a-tetrahydro-1,5-(epoxymethano) cyclopenta[c]pyran-3-yl)methyl 9-oxo-9H-fluorene-4-carboxylate |
| Compound 17 | 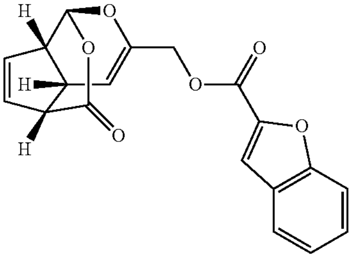 [SMILES: O=C(OCC1=C[C@H]2[C@@H]3C=C[C@H]2C(=O)O[C@@H]3O1)c1cc2ccccc2o1] | ((1S,4aS,5R,7aS)-8-oxo-1,4a,5,7a-tetrahydro-1,5-(epoxymethano) cyclopenta[c]pyran-3-yl)methyl-benzofuran-2-carboxylate |
| Compound 18 | 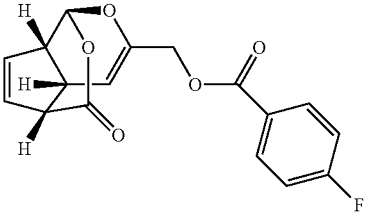 [SMILES: O=C(OCC1=C[C@H]2[C@@H]3C=C[C@H]2C(=O)O[C@@H]3O1)c1ccc(F)cc1] | ((1S,4aS,5R,7aS)-8-oxo-1,4a,5,7a-tetrahydro-1,5-(epoxymethano) cyclopenta[c]pyran-3-yl)methyl 4-fluorobenzoate |
| Compound 19 | 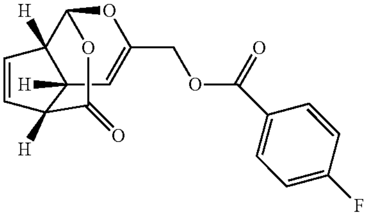 [SMILES: O=C(OCC1=C[C@H]2[C@@H]3C=C[C@H]2C(=O)O[C@@H]3O1)c1ccc(F)cc1] | ((1S,4aS,5R,7aS)-8-oxo-1,4a,5,7a-tetrahydro-1,5-(epoxymethano) cyclopenta[c]pyran-3-yl)methyl 4-chlorobenzoate |
| Compound 20 | 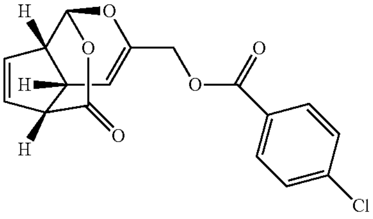 [SMILES: O=C(OCC1=C[C@H]2[C@@H]3C=C[C@H]2C(=O)O[C@@H]3O1)c1ccc(Cl)cc1] | ((1S,4aS,5R,7aS)-8-oxo-1,4a,5,7a-tetrahydro-1,5-(epoxymethano) cyclopenta[c]pyran-3-yl)methyl 4-iodobenzoate |

-continued

| Example | Structure | IUPAC name |
|---|---|---|
| Compound 21 | 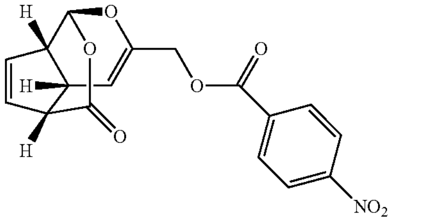 [SMILES: O=C(OCC1=C[C@H]2[C@@H]3C=C[C@H]2C(=O)O[C@@H]3O1)c1ccc([N+](=O)[O-])cc1] | (1S,4aS,5R,7aS)-8-oxo-1,4a,5,7a-tetrahydro-1,5-(epoxymethano) cyclopenta[c]pyran-3-yl)methyl 4-nitrobenzoate |
| Compound 22 | 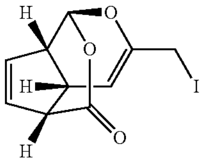 [SMILES: O=C1O[C@@H]2OC(CI)=C[C@H]3[C@@H]2C=C[C@@H]13] | (1S,4aS,5R,7aS)-3-(iodomethyl)-1,4a,5,7a-tetrahydro-1,5-(epoxy-methano)cyclopenta[c]pyran-8-one |
| Compound 23 | 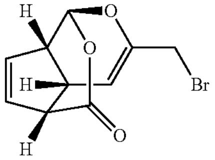 [SMILES: O=C1O[C@@H]2OC(CBr)=C[C@H]3[C@@H]2C=C[C@@H]13] | (1S,4aS,5R,7aS)-3-(bromomethyl)-1,4a,5,7a-tetrahydro-1,5-(epoxy-methano)cyclopeata[c]pyran-8-one |
| Compound 24 | 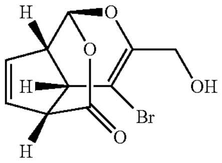 [SMILES: O=C1O[C@@H]2OC(CO)=C(Br)[C@H]3[C@@H]2C=C[C@@H]13] | (1S,4aS,5R,7aS)-4-bromo-3-(hydroxymethyl)-1,4a,5,7a-tetrahydro-1,5-(epoxymethano) cyclopenta[c]pyran-8-one |
| Compound 25 | 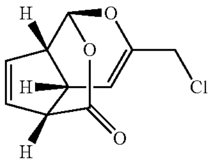 [SMILES: O=C1O[C@@H]2OC(CCl)=C[C@H]3[C@@H]2C=C[C@@H]13] | (1S,4aS,5R,7aS)-3-(chloromethyl)-1,4a,5,7a-tetrahydro-1,5-(epoxy-methano)cyclopenta[c]pyran-8-one |

In the present invention, the "pharmaceutically acceptable salt" refers to salts commonly used in the pharmaceutical industry. For example, the pharmaceutically acceptable salt includes inorganic ion salts prepared from calcium, potassium, sodium, magnesium, etc.; inorganic acid salts prepared from hydrochloric acid, nitric acid, phosphoric acid, hydrobromic acid, iodic acid, perchloric acid, sulfuric acid, etc.; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid, etc.; amino acid salts prepared from glycine, arginine, lysine, etc.; and amine salts prepared from trimethylamine, triethylamine, ammonia, pyridine, picoline, etc. However, the types of salts meant in the present invention are not limited to these listed salts.

Use of Compound of Chemical Formula 1

The present invention provides a use of a compound represented by Chemical Formula 1 below, an isomer thereof or a pharmaceutically acceptable salt thereof.

[Chemical Formula 1]

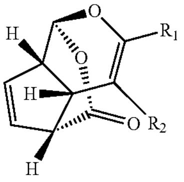

In Chemical Formula 1 above, $R_1$ is $—C(=O)R_a$, $—CH_2R_b$ or $—CH=NCH_2C≡CH$, $R_a$ is any one selected from the group consisting of —H, —OH, $—OCH_3$, $—OCH_2CH_3$, and $—OCH_2CH_2CH_3$, $R_b$ is $—OR_{b1}$ or halogen, $R_{b1}$ is any one selected from the group consisting of —H, $—CH_3$, $—CH_2CH_3$, $—CH_2CH_2CH_3$, $—C(=O)R_{b11}$,

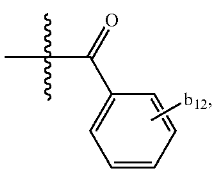

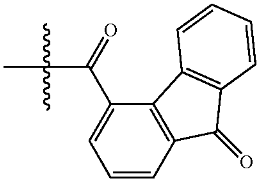

,

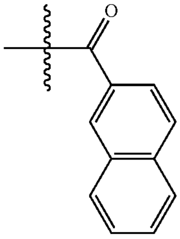

and

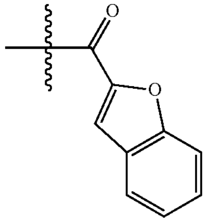

, $R_{b11}$ is a straight-chain or branched-chain $C_1$-$C_5$ alkyl group or a straight-chain or branched-chain $C_6$-$C_{12}$ alkenyl group containing at least one double or triple bond between carbons, $R_{b12}$ is any one selected from the group consisting of —H, $—CH_3$, $—CH_2CH_3$, $—CH_2CH_2CH_3$, halogen, $—OCH_3$, $—OCH_2CH_3$, $—NO_2$ and a phenyl group, and $R_2$ is —H or halogen.

The present invention provides a pharmaceutical composition including the compound represented by Chemical Formula 1, an isomer thereof or a pharmaceutically acceptable salt thereof.

The present invention provides a brain neuroinflammation inhibitor including the compound represented by Chemical Formula 1, an isomer thereof or a pharmaceutically acceptable salt thereof.

The compounds according to the present invention exhibit excellent effects in inhibiting brain neuroinflammation and may be used for various therapeutic uses.

The present invention provides a pharmaceutical composition for preventing or treating neuroinflammatory brain diseases including the compound represented by Chemical Formula 1, an isomer thereof, or a pharmaceutically acceptable salt thereof as an active ingredient.

In the present invention, non-limiting examples of the neuroinflammatory brain diseases may include Parkinson's disease, Huntington's disease, Alzheimer's disease, mild cognitive impairment, senile dementia, amyotrophic lateral sclerosis, Spinocerebellar Atrophy, Tourette's Syndrome, Friedrich's Ataxia, Machado-Joseph's disease, Lewy Body Dementia, Dystonia, Progressive Supranuclear Palsy, Frontotemporal Dementia, etc.

The pharmaceutical composition of the present invention may further include at least one pharmaceutically acceptable carrier in addition to the compound represented by Chemical Formula 1, the isomer thereof or the pharmaceutically acceptable salt thereof for administration. The pharmaceutically acceptable carrier may be used by mixing saline, sterile water, Ringer's solution, buffered saline, a dextrose solution, a maltodextrin solution, glycerol, ethanol, and at least one of these ingredients, and if necessary, other conventional additives such as antioxidants, buffers, bacteriostats, etc. may be added. In addition, the pharmaceutical composition may be prepared in injectable formulations such as an aqueous solution, a suspension, and an emulsion, pills, capsules, granules, or tablets by further adding a diluent, a dispersant, a surfactant, a binder, and a lubricant.

Accordingly, the pharmaceutical composition of the present invention may be patches, liquids, pills, capsules, granules, tablets, suppositories or the like. These formulations may be prepared by conventional methods used for formulation in the art or by methods disclosed in Remington's Pharmaceutical Science (latest edition), Mack Publishing Company, Easton PA, and may be prepared into various formulations according to each disease or an ingredient.

The pharmaceutical composition of the present invention may be administered orally or parenterally (e.g., intravenously, subcutaneously, intraperitoneally or topically applied) according to a desired method, and the range of the dose may vary depending on the body weight, age, sex, and health condition of a patient, a diet, an administration time, an administration method, an excretion rate, the type and severity of a disease, and the like. The daily dose of the compound of Chemical Formula 1 of the present invention is about 0.01 to 1000 mg/kg, preferably 0.1 to 100 mg/kg, and may be administered once or several times a day.

The pharmaceutical composition of the present invention may further include at least one active ingredient having the same or similar efficacy in addition to the compound represented by Chemical Formula 1, the isomer thereof or the pharmaceutically acceptable salt thereof.

The present invention provides a method for treating or preventing neuroinflammatory brain diseases including administering a therapeutically effective amount of the compound represented by Chemical Formula 1, an isomer thereof, or a pharmaceutically acceptable salt thereof to mammals, including humans.

As used in the present invention, the term "therapeutically effective amount" refers to an amount of the compound represented by Chemical Formula 1, the isomer thereof, or the pharmaceutically acceptable salt thereof that is effective in preventing or treating neuroinflammatory brain diseases.

The treatment method of the present invention includes not only treating the disease itself before the onset of symptoms, but also inhibiting or avoiding symptoms thereof, by administering the compound of Chemical Formula 1. In the management of the diseases, a prophylactic or therapeutic dose of a specific active ingredient will vary according to the nature and severity of the disease or condition, and a route by which the active ingredient is administered. The dose and the dose frequency will vary according to the age, body weight and response of an individual patient. A suitable dosage regimen may be easily selected by those skilled in the art who certainly consider these factors. In addition, the treatment method of the present invention may further include administering a therapeutically effective amount of an additional active agent to help in treating the diseases together with the compound of Chemical Formula 1, and the additional active agent may exhibit a synergistic or auxiliary effect together with the compound of Chemical Formula 1.

The present invention provides a food composition for preventing or ameliorating neuroinflammatory brain diseases including the compound represented by Chemical Formula 1, an isomer thereof, or a pharmaceutically acceptable salt thereof as an active ingredient.

The food composition of the present invention may be used as a health functional food. The "health functional food" refers to food produced and processed using raw materials or ingredients with functionality, which are useful for the human body according to the Art on Health Functional Foods No. 6727, and the "functionality" means intake for adjusting nutrients for the structures and functions of the human body or obtaining an useful effect on health applications such as physiological actions.

The food composition of the present invention may include conventional food additives, and the suitability as the "food additive" is determined by the specifications and standards for the corresponding item in accordance with the general rules of the Food Additive Codex, general test methods, and the like approved by the Food and Drug Administration, unless otherwise specified.

The food composition of the present invention may include the compound of Chemical Formula 1 in an amount of 0.01 to 95 wt %, preferably 1 to 80 wt %, based on the total weight of the composition, for the purpose of preventing and/or ameliorating the neuroinflammatory brain diseases. In addition, the food composition may be produced and processed in the form of tablets, capsules, powders, granules, liquids, pills, beverages, and the like, for the purpose of preventing and/or ameliorating cancer-related diseases.

In addition, the present invention provides a use of the compound represented by Chemical Formula 1, an isomer thereof or a pharmaceutically acceptable salt thereof for preparation of a drug for the treatment of neuroinflammatory brain diseases. For the preparation of the drug, the compound of Chemical Formula 1 may be mixed with acceptable adjuvants, diluents, carriers and the like, and may be prepared as a complex preparation together with other active agents to have a synergistic action of the active ingredients.

Further, the present invention provides a food composition for enhancing a cognitive function including a compound represented by Chemical Formula 1, an isomer thereof, or a pharmaceutically acceptable salt thereof as an active ingredient.

The present invention also includes the following embodiments:

a compound represented by Chemical Formula 1, an isomer thereof or a pharmaceutically acceptable salt thereof as defined in any embodiment described herein, for use as a drug;

a compound represented by Chemical Formula 1, an isomer or a pharmaceutically acceptable salt thereof, as defined in any embodiment described herein, for use in the prevention or treatment of neuroinflammatory brain diseases discussed herein;

a method for preventing or treating neuroinflammatory brain diseases including administering a compound represented by Chemical Formula 1, an isomer or a pharmaceutically acceptable salt thereof in a therapeutically effective amount as defined in any embodiment described herein to a subject in need thereof;

a compound represented by Chemical Formula 1, an isomer or a pharmaceutically acceptable salt thereof, as defined in any embodiment described herein, for preparation of a drug for the treatment of neuroinflammatory brain diseases; and a brain neuroinflammation inhibitor including a compound represented by Chemical Formula 1, an isomer thereof or a pharmaceutically acceptable salt thereof as defined in any embodiment described herein.

As used herein, the term "subject" refers to a subject in need of treatment for diseases, and more particularly, may mean mammals such as humans or non-human primates, mice, dogs, cats, horses and cattle, but is not limited thereto.

Use of Compound 26 of Chemical Formula 2

The present invention has also been made in an effort to provide a use of Compound 26 represented by Chemical Formula 2 below, an isomer thereof or a pharmaceutically acceptable salt thereof.

[Chemical Formula 2]

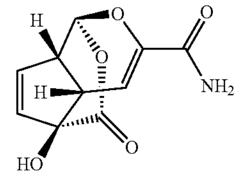

Compound 26 of Chemical Formula 2 above is named (1S,4aS,5R,7aS)-5-hydroxy-8-oxo-1,4a,5,7a-tetrahydro-1,5-(epoxymethano)cyclopenta[c]pyran-3-carboxamide and has an excellent effect of inhibiting brain neuroinflammation, and thus may be used for various therapeutic uses.

Therefore, the present invention provides a pharmaceutical composition for preventing or treating neuroinflammatory brain diseases including Compound 26 of Chemical Formula 2, an isomer thereof, or a pharmaceutically acceptable salt thereof as an active ingredient.

Further, the present invention provides a method for preventing or treating neuroinflammatory brain diseases including administering a compound represented by Chemical Formula 2, an isomer or a pharmaceutically acceptable salt thereof in a therapeutically effective amount as defined in any embodiment described herein to a subject in need thereof.

Specific expressions of all terms related to the use of Compound 26 of Chemical Formula 2 are defined in the same manner as the meanings of the terms defined in the use of the compound of Chemical Formula 1 described above.

All examples, isomers thereof, or pharmaceutically acceptable salts thereof may be claimed individually or grouped together in any combination with any number of all respective embodiments described herein.

Matters mentioned in the composition, the use, and the treatment method of the present invention are applied equally unless contradict each other.

Advantageous Effects

According to the present invention, the compound represented by Chemical Formula 1, the isomer thereof or the pharmaceutically acceptable salt thereof exhibits an excellent effect of inhibiting brain neuroinflammation and an excellent effect of treating diseases such as neuroinflammatory brain diseases.

DESCRIPTION OF DRAWINGS

FIG. 1 is a diagram illustrating separation method and process of Compound 1.

FIG. 2 shows $^{1}H$ NMR and $^{13}C$ NMR spectra of Compound 1.

FIG. 3 shows a HRMS spectrum of Compound 1.

FIG. 4 is a diagram illustrating $^{1}H$ NMR and $^{13}C$ NMR shift values and a correlation between COZY and HMBC of Compound 1.

FIG. 5 shows a HMBC spectrum of Compound 1.

FIG. 6 illustrates an absolute structure of Compound 1 through X-ray diffraction analysis.

FIG. 7 shows a semi-synthetic derivative example and $^{1}H$ NMR and $^{13}C$ NMR spectra of Compound 2.

FIG. 8 shows a semi-synthetic derivative example and $^{1}H$ NMR and $^{13}C$ NMR spectra of Compound 3.

FIG. 9 shows a semi-synthetic derivative example and $^{1}H$ NMR and $^{13}C$ NMR spectra of Compound 4.

FIG. 10 shows a semi-synthetic derivative example and $^1H$ NMR and $^{13}C$ NMR spectra of Compound 5.

FIG. 11 shows a semi-synthetic derivative example and $^1H$ NMR and $^{13}C$ NMR spectra of Compound 6.

FIG. 12 shows a semi-synthetic derivative example and $^1H$ NMR and $^{13}C$ NMR spectra of Compound 7.

FIG. 13 shows a semi-synthetic derivative example and $^1H$ NMR and $^{13}C$ NMR spectra of Compound 8.

FIG. 14 shows a semi-synthetic derivative example and $^1H$ NMR and $^{13}C$ NMR spectra of Compound 9.

FIG. 15 shows a semi-synthetic derivative example and $^1H$ NMR and $^{13}C$ NMR spectra of Compound 10.

FIG. 16 shows a semi-synthetic derivative example and $^1H$ NMR and $^{13}C$ NMR spectra of Compound 11.

FIG. 17 shows a semi-synthetic derivative example and $^1H$ NMR and $^{13}C$ NMR spectra of Compound 12.

FIG. 18 shows a semi-synthetic derivative example and $^1H$ NMR and $^{13}C$ NMR spectra of Compound 13.

FIG. 19 shows a semi-synthetic derivative example and $^1H$ NMR and $^{13}C$ NMR spectra of Compound 14.

FIG. 20 shows a semi-synthetic derivative example and $^1H$ NMR and $^{13}C$ NMR spectra of Compound 15.

FIG. 21 shows a semi-synthetic derivative example and $^1H$ NMR and $^{13}C$ NMR spectra of Compound 16.

FIG. 22 shows a semi-synthetic derivative example and $^1H$ NMR and $^{13}C$ NMR spectra of Compound 17.

FIG. 23 shows a semi-synthetic derivative example and $^1H$ NMR and $^{13}C$ NMR spectra of Compound 18.

FIG. 24 shows a semi-synthetic derivative example and $^1H$ NMR and $^{13}C$ NMR spectra of Compound 19.

FIG. 25 shows a semi-synthetic derivative example and $^1H$ NMR and $^{13}C$ NMR spectra of Compound 20.

FIG. 26 shows a semi-synthetic derivative example and $^1H$ NMR and $^{13}C$ NMR spectra of Compound 21.

FIG. 27 shows a semi-synthetic derivative example and $^1H$ NMR and $^{13}C$ NMR spectra of Compound 22.

FIG. 28 shows a semi-synthetic derivative example and $^1H$ NMR and $^{13}C$ NMR spectra of Compounds 23 and 24.

FIG. 29 shows a semi-synthetic derivative example and $^1H$ NMR and $^{13}C$ NMR spectra of Compound 25.

FIG. 30 shows (a) a graph of changes in NO release amount induced by LPS, (b) a cytotoxicity test graph, (c) expression inhibition of proteins iNOS and COX-2, and (d) expression inhibition of genes of iNOS and COX-2 and genes of inflammation-mediating cytokines TNF-α, IL1-β, and IL-6, after treatment with Compound 1 and LPS.

FIG. 31 shows (a) a graph of changes in NO release amount induced by LPS (Compounds 50 μM), (b) a cytotoxicity test graph (Compounds 50 PM), (c) a graph of changes in NO release amount induced by LPS (Compounds 25 μM), and (d) a cytotoxicity test graph (Compounds 25 μM), after treatment with LPS of Compounds 1 to 4.

FIG. 32 shows (a) a graph of changes in NO release amount induced by LPS (Compounds 50 μM), (b) a cytotoxicity test graph (Compounds 50 PM), (c) a graph of changes in NO release amount induced by LPS (Compounds 25 μM), and (d) a cytotoxicity test graph (Compounds 25 μM), after treatment with LPS of Compounds 5 to 11.

FIG. 33 shows (a) a graph of changes in NO release amount induced by LPS and (b) a cytotoxicity test graph of Compounds 12 to 21.

FIG. 34 shows (a) a cytotoxicity test graph and (b) a graph of changes in NO release amount induced by LPS of Compounds 22 to 25 [each Compound has a condition of concentrations of 50, 100, and 200 μM in sequence].

FIG. 35 shows (a) a graph of changes in NO release amount induced by LPS, (b) a cytotoxicity test graph, (c) expression inhibition of proteins iNOS and COX-2, and (d) expression inhibition of genes of iNOS and COX-2 and genes of inflammation-mediating cytokines TNF-α, IL1-β, and IL-6 of Compound 4.

FIG. 36 shows (a) a graph of changes in NO release amount induced by LPS, (b) a cytotoxicity test graph, (c) expression inhibition of proteins iNOS and COX-2, and (d) expression inhibition of genes of iNOS and COX-2 and genes of inflammation-mediating cytokines TNF-α, IL1-β, and IL-6 of Compound 6.

FIG. 37 shows (a) a graph of changes in NO release amount induced by LPS and (b) a cytotoxicity test graph of Compound 26.

MODE OF THE INVENTION

Hereinafter, Examples of the present invention will be described in detail so as to easily implement those skilled in the art. However, the present invention may be embodied in many different forms and are not limited to embodiments described herein.

Experimental Devices 1D ($^1H$ and $^{13}C$), and 2D (COSY, ROESY, HSQC, and HMBC) NMR spectra were obtained using Varian Unity 500 MHz and Bruker 600 MHz spectrometers. UV spectra were obtained using a Shimadzu UV-1650PC spectrophotometer. IR spectra were obtained using a JASCO FT/IR-4100 spectrophotometer. Optical rotation was measured using a Rudolph Research Analytical (Autopol III) polarimeter. High-resolution (HR) ESIMS was recorded using a Waters Synapt HDMS LC/MS mass spectrometer. HPLC was performed using an RI-101 (Shodex) detector and a PrimeLine Binary pump. HPLC was performed on a Semi-preparative ODS column (YMC-Pack-ODS-A, 250×10 mm, i.d., 5 μm) and an Analytical ODS column (YMC-Pack-ODS-A, 250×4.6 mm, i.d., 5 μm).

Example 1. Preparation of Compound (1S,4aS,5R,7aS)-3-(hydroxymethyl)-1,4a,5,7a-tetrahydro-1,5-(epoxymethano)cyclopenta[c]pyran-8-one and Characteristic Analysis of Compound of Example 1

(1) Isolation and Mass Culture of Strain 151KO-065

In January 2015, a strain 151KO-065 was isolated from mangroves collected in the Kosrae Island. As a result of 16S rRNA gene sequencing (GenBank registration number KX078377), it was confirmed that the strain was the genus *Streptomyces.*

The isolated strain 151KO-065 was cultured in a Bennett (BN) agar medium at 28° C. for 7 days, and thereafter, the strain was inoculated into a flask containing 50 mL of a BN broth (containing 10 g glucose, 1 g yeast extract, 2 g tryptone, 1 g beef extract, 5 g glycerol, and 32 g NaCl in 1 L distilled water) and cultured at 130 rpm and 28° C. for 7 days. 10 mL of the culture was inoculated into a 2 L flask containing the BN medium (1 L) and cultured for 4 days under the same conditions. For mass culture, the culture was inoculated using a 2 L flask containing 1 L of the culture medium and cultured in 70 L of the BN medium in a 100 L fermentor. 70 L of the culture was cultured at 28° C. for 4 days.

The *Streptomyces malaysience* 151KO-065 was deposited on Feb. 5, 2020 and received the deposit number KCTC 14126BP.

(2) Isolation of Compound of Example 1

The culture (total 70 L) was centrifuged to separate cells and a supernatant, and the supernatant was extracted with ethyl acetate (EtOAc, 70LX2) at room temperature. The ethyl acetate extract was dried to obtain a crude extract (10 g). The crude extract was fractioned according to polarity using flash column chromatography using ODS while eluting stepwise with a combination of $MeOH/H_2O$ (1:4, 2:3, 3:2, 4:1, and 100% MeOH).

The fractions eluted at a $MeOH/H_2O$ ratio of 1:4 was subjected to isocratic elution with a 10% methanol aqueous solution and purified by Semipreparative ODS HPLC (YMC-Pack-ODS-A, 250×10 mm, i.d., 5 μm, flow rate 4.0 mL/min, RI detector) to obtain Compound of Example 1 in the form of viscous light yellow oil (FIG. 1).

Compound 1: (1S,4aS,5R,7aS)-3-(hydroxymethyl)-1,4a,5,7a-tetrahydro-1,5-(epoxymethano)cyclopenta[c]pyran-8-one Light yellow oil: $[\alpha]_D^{25}$ −173.32 (c 0.1, $CH_{30}H$); UV (MeOH) $\lambda_{max}$ (log ε) 205 (1.02) nm; HRESIMS m/z 217.0477 $[M+Na]^+$, calcd for $C_{10}H_{10}O_4Na$, 217.0477.

$^1H$ NMR ($CD_3OD$, 500 MHz) and $^{13}C$ NMR ($CD_3OD$, 125 MHz) results of Compound of Example 1 were shown in Table 1 below (FIG. 2).

TABLE 1

| | Compound 1 | |
|---|---|---|
| no. | $\delta_H$ (J. Hz) | $\delta_C$ type |
| 1 | 3.29, dd (5.0, 3.5) | 52.3 CH |
| 2 | 5.82 br t (1.5) | 96.1 CH |
| 3 | | 151.2 C |
| 4 | 5.26, d (5.5) | 97.4 CH |
| 5 | 3.01, dd (10.0, 4.5) | 41.6 CH |
| 6 | 2.74, ddd (5.0, 3.0, 2.0) | 39.2 CH |
| 7 | 6.47, dd (5.5, 3.0) | 135.2 CH |
| 8 | 6.38, dd (6.0, 3.0) | 136.4 CH |
| 9 | 3.98, s | 60.3 $CH_2$ |
| 10 | | 170.6 C |

(3) Planar Structure Analysis of Compound of Example 1

Compound 1 was determined to have the molecular formula of $C_{10}H_{10}O_4$ according to a result of HRESIMS analysis (m/z 217.0477 $[M+Na]^+$, 217.0477 calculated value) (FIG. 3). As a result of analyzing $^{13}C$ NMR data and HSQC spectrum of Compound 1, one methylene ($\delta_H$ 3.98), four methines ($\delta_H$ 2.74, 3.01, 3.29, 5.82), three olefin hydrogens ($\delta_H$ 5.26, 6.38, 6.47) and two quaternary carbons ($\delta_C$ 151.2, 170.6) bound with oxygens were confirmed. The planar structure of the compound was determined using 2D NMR data and $^1H$-$^1H$ COZY and HMBC spectra (FIGS. 4 and 5). It was confirmed that Compound 1 had a cyclopentine ring structure by a COZY correlation of H-4, H-5, H-6, H-7, H-8, H-1, and H-2 and had another ring through an HMBC correlation between H-2, H-4, H-5, and C-3. The acetal structure was confirmed by an HMBC correlation between singlet methine H-2 and C-3 and C-10, and a correlation from H-2 and H-5 to carbonyl carbon C-10 showed that the carbonyl group was linked to C-2 and C-6 in the form of an ester bridge. Finally, it was confirmed that the remaining singlet methylene H-9 was linked to C-3 through an HMBC correlation between H-9, C-3, and C-4.

(4) Absolute Array Analysis of Compound of Example 1

The relative structure was first determined by analyzing the ROESY correlation of Compound of Example 1, and then the absolute array was determined using comparative analysis of intrinsic optical rotation and X-ray diffraction analysis. First, in the ROESY correlation between H-1, H-2, H-5, and H-6, it was confirmed that four protons existed on the same side and an ester bridge was disposed on an opposite side. It was confirmed that both the intrinsic optical rotation of a structurally similar (−)-echinosporin literature and the intrinsic optical rotation of Compound 1 had a (−) value. Next, Compound of Example 1 was tried for use in X-ray diffraction analysis, but was not formed. For crystallization, 4-bromobenzoyl chloride was introduced into primary alcohol of Compound 1 to obtain Compound of Example 4. In the case of Compound of Example 4, a crystal was obtained, and as a result of structural analysis by performing an X-ray diffraction experiment on Compound of Example 4, it was determined to have an absolute array shown in FIG. 6.

Examples 2 to 25. Preparation of Compounds 2 to 25

Compounds of Examples 2 to 25 below were prepared by semi-synthesis based on the compound of Example 1 prepared in Example 1 above, and prepared using an appropriate commercially available starting material, or using a preparation method well known to those skilled in the art. These compounds were purified using methods well known to those skilled in the art, which may include silica gel chromatography, HPLC, or recrystallization from a reaction mixture.

Example 2. Synthesis of Compound of Example 2 (((1S,4aS,5R,7aS)-8-oxo-1,4a,5,7a-tetrahydro-1,5-(epoxymethano)cyclopenta[c]pyran-3-yl)methyl acetate)

The compound (10 mg, 0.052 mmol) of Example 1 was dissolved in 400 μL of pyridine, and then stirred and reacted at room temperature for 1 hour using 8 μL (0.078 mmol) of acetic anhydride and 4-dimethylaminopyridine in a catalytic amount. After completion of the reaction, the solvent was removed through vacuum drying, and Compound of Example 2 was obtained using silica column chromatography (hexane:ethyl acetate=3:1, volume ratio) (FIG. 7).

$^1H$-NMR (500 MHz, Chloroform-d) $\delta_H$ ppm (J, Hz): 6.36 (1H, br), 6.31 (1H, br), 5.72 (1H, br s), 5.23 (1H, d, 6.0), 4.48 (2H, s), 3.27 (1H, br dd, 4.5), 2.94 (1H, br dd, 4.5), 2.69 (1H, br dd), 2.03 (3H, s), $^{13}C$-NMR (125 MHz, Chloroform-d) $\delta_C$ ppm: 170.1, 168.5, 146.7, 136.7, 134.5, 101.2, 95.5, 62.2, 51.9, 41.4, 38.7, 20.6, LRMS m/z 236.7 $[M+H]^+$.

Example 3. Synthesis of Compound of Example 3 ((1S,4aS,5R,7aS)-3-(methoxymethyl)-1,4a,5,7a-tetrahydro-1,5-(epoxymethano)cyclopenta[c]pyran-8-one)

The compound (10 mg, 0.052 mmol) of Example 1 was dissolved in 400 μL of dimethylformamide (DMF), and then stirred and reacted at 0° C. for 5 hours by adding 6.25 mg (0.156 mmol) of sodium hydride (NaH) and 10 μL (0.156 mmol) of iodomethane (MeI). After adding lithium chloride to remove dimethylformamide (DMF), an organic layer was extracted with ethyl acetate (EA) and dried under reduced pressure. The obtained mixture was separated and purified to a desired result product using silica column chromatography (hexane:ethyl acetate=2:1, volume ratio) to obtain Compound of Example 3 (FIG. 8). $^1$H-NMR (500 MHz, Chloroform-d) $\delta_H$ ppm (J, Hz): 6.37 (1H, dd, 5.5, 3.0), 6.33 (1H, dd, 5.5, 3.5), 5.75 (1H, br s), 5.21 (1H, d, 5.5), 3.92, 3.81 (2H, d, 13.0), 3.31 (3H, s), 3.30 (1H, overlapped), 2.97 (1H, dd, 10.0, 5.0), 2.71 (1H, dd, 5.0, 2.5), $^{13}$C-NMR (125 MHz, Chloroform-d) $\delta_C$ ppm: 169.1, 148.2, 136.8, 134.6, 100.2, 95.7, 70.8, 57.9, 52.2, 41.8, 39.0, LRMS m/z 208.9 [M+H]$^+$.

Example 4. Synthesis of Compound of Example 4 (((1S,4aS,5R,7aS)-8-oxo-1,4a,5,7a-tetrahydro-1,5-(epoxymethano)cyclopenta[c]pyran-3-yl)methyl 4-bromobenzoate)

The compound (10 mg, 0.052 mmol) of Example 1 was dissolved in 400 μL of dichloromethane, and then stirred and reacted at room temperature for 1 hour using 10.7 mg (0.052 mmol) of 4-bromobenzoyl chloride and 4-dimethylaminopyridine (DMAP) in a catalytic amount. After completion of the reaction, the solvent was removed through vacuum drying, and Compound of Example 4 was obtained using silica column chromatography (hexane:ethyl acetate=4:1, volume ratio) (FIG. 9). $^1$H-NMR (500 MHz, Chloroform-d) $\delta_H$ ppm (J, Hz): 7.90 (2H, d, 8.5), 7.57 (2H, d, 8.5), 6.39 (1H, br), 6.37 (1H, br), 5.79 (1H, br s), 5.35 (1H, d, 5.5), 4.80, 4.75 (2H, d, 13.0), 3.35 (1H, br dd, 3.5), 3.01 (1H, br dd, 4.5), 2.75 (1H, br dd), $^{13}$C-NMR (125 MHz, Chloroform-d) $\delta_C$ ppm: 168.8, 165.2, 146.9, 137.0, 134.6, 13.8, 131.8, 131.3, 131.3, 128.5, 128.4, 101.5, 95.7, 62.9, 52.1, 41.7, 39.0, LRMS m/z 378.8 [M+H]$^+$.

Example 5. Synthesis of Compound of Example 5 ((1S,4aS,5R,7aS)-8-oxo-1,4a,5,7a-tetrahydro-1,5-(epoxymethano)cyclopenta[c]pyran-3-carboxylic acid)

The compound (10 mg, 0.052 mmol) of Example 1 was dissolved in 1 mL of dimethylformamide (DMF), and then stirred and reacted at room temperature for 16 hours by adding 98 mg (0.26 mmol) of pyridinium dichromate (PDC). After adding lithium chloride to remove dimethylformamide (DMF), an organic layer was extracted with ethyl acetate (EA) and dried under reduced pressure. The obtained mixture was separated and purified to a desired result product using silica column chromatography (dichloromethane: methanol=5:1, volume ratio) to obtain Compound of Example 5 (FIG. 10). $^1$H-NMR (500 MHz, $D_2O$) $\delta_H$ ppm (J, Hz): 6.51 (1H, dd, 5.5, 3.0), 6.40 (1H, dd, 5.5, 3.0), 6.17 (1H, d, 5.5), 6.01 (1H, br s), 3.46 (1H, br dd, 4.0), 3.02 (1H, br dd, 4.5), 2.75 (1H, br dd), $^{13}$C-NMR (125 MHz, $D_2O$) $\delta_C$ ppm: 173.9, 168.5, 143.9, 136.0, 135.3, 108.2, 96.5, 51.8, 41.5, 38.0, LRMS m/z 208.9 [M+H]$^+$.

Example 6. Synthesis of Compound of Example 6 ((1S,4aS,5R,7aS)-8-oxo-1,4a,5,7a-tetrahydro-1,5-(epoxymethano)cyclopenta[c]pyran-3-carbaldehyde)

The compound (20 mg, 0.104 mmol) of Example 1 was dissolved in 600 μL of dichloromathane, and then stirred and reacted at room temperature for 1 hour by adding 65 mg (0.156 mmol) of dess-martin periodinane (DMP). After completion of the reaction, the solvent was removed through vacuum drying, and Compound of Example 6 was obtained using silica column chromatography (hexane:ethyl acetate=2:1, volume ratio) (FIG. 11). $^1$H-NMR (500 MHz, Chloroform-d) (H ppm (J, Hz) 9.26 (1H, s), 6.42 (1H, dd, 5.5, 3.0), 6.39 (1H, dd, 5.5, 3.0), 6.22 (1H, d, 6.0), 5.89 (1H, br s), 3.44 (1H, dd, 5.0, 3.5), 3.24 (1H, dd, 5.0, 4.5), 2.80 (1H, dd, 5.0, 3.0), $^{13}$C-NMR (125 MHz, Chloroform-d) $\delta_C$ ppm: 185.0, 167.6, 148.5, 136.8, 134.2, 199.8, 95.5, 51.6, 42.0, 38.6, LRMS m/z 192.7 [M+H]$^+$.

Example 7. Synthesis of Compound of Example 7 (((1S,4aS,5R,7aS)-8-oxo-1,4a,5,7a-tetrahydro-1,5-(epoxymethano)cyclopenta[c]pyran-3-yl)methyl benzoate)

The synthesis method was the same as the synthesis method of the compound of Example 4, but Compound of Example 7 was obtained using benzoyl chloride (0.052 mmol) instead of 4-bromobenzoyl chloride (FIG. 12). $^1$H-NMR (500 MHz, Chloroform-d) $\delta_H$ ppm (J, Hz): 8.04 (2H, d, 6.5), 7.55 (1H, t, 6.5), 7.42 (2H, t, 6.5), 6.38 (1H, br dd), 6.35 (1H, br dd), 5.78 (1H, br s), 5.35 (1H, d, 5.0), 4.80, 4.76 (2H, d, 11.5), 3.34 (1H, br dd), 2.99 (1H, br dd, 3.5), 2.74 (1H, br dd), $^{13}$C-NMR (125 MHz, Chloroform-d) $\delta_C$ ppm: 168.8, 165.8, 147.0, 136.9, 134.6, 133.1, 129.7, 129.7, 129.5, 128.4, 128.4, 101.0, 95.6, 62.6, 52.1, 41.7, 38.9, LRMS m/z 321.0 [M+Na]$^+$.

Example 8. Preparation of Compound of Example 8 (((1S,4aS,5R,7aS)-8-oxo-1,4a,5,7a-tetrahydro-1,5-(epoxymethano)cyclopenta[c]pyran-3-yl)methylundec-10-enoate)

The synthesis method was the same as the synthesis method of the compound of Example 4, but Compound of Example 8 was obtained using 10-undecenoyl chloride (0.052 mmol) instead of 4-bromobenzoyl chloride (FIG. 13). $^1$H-NMR (500 MHz, Chloroform-d) $\delta_H$ ppm (J, Hz): 6.37 (1H, dd, 5.0, 3.5), 6.34 (1H, dd, 5.5, 3.5), 5.77 (1H, m), 5.74 (1H, br s), 5.25 (1H, d, 6.0), 4.95 (1H, d, 17.0), 4.89 (1H, d, 10.0), 4.51 (2H, s), 3.31 (1H, br dd, 3.0), 2.97 (1H, br dd, 5.5), 2.71 (1H, br dd), 2.31 (2H, t, 7.5), 1.99 (2H, dt, 7.5, 7.0), 1.59 (2H, m), 1.2-1.4 (10H, overlapped), $^{13}$C-NMR (125 MHz, Chloroform-d) $\delta_C$ ppm: 173.1, 168.7, 147.0, 139.0, 136.9, 134.5, 114.0, 101.0, 95.6, 62.0, 52.0, 41.6, 38.9, 34.0, 33.7, 29.2, 29.1, 28.9, 28.9, 28.8, 24.7, LRMS m/z 361.0 [M+H]$^+$.

Example 9. Preparation of Compound of Example 9 (((1S,4aS,5R,7aS)-8-oxo-1,4a,5,7a-tetrahydro-1,5-(epoxymethano)cyclopenta[c]pyran-3-yl)methyl 2-methyl butanoate)

The synthesis method was the same as the synthesis method of the compound of Example 4, but Compound of Example 9 was obtained using 2-methylbutyryl chloride (0.052 mmol) instead of 4-bromobenzoyl chloride (FIG. 14). $^1$H-NMR (500 MHz, Chloroform-d) $\delta_H$ ppm (J, Hz): 6.37 (1H, dd, 5.5, 3.0), 6.34 (1H, 5.5, 3.5), 5.75 (1H, br s), 5.25 (1H, d, 5.5), 4.53 (2H, s), 3.31 (1H, br dd, 4.0), 2.97 (1H, br dd, 5.0), 2.70 (1H, br dd), 2.39 (1H, m), 1.66, 1.46 (2H, m), 1.12 (3H, d, 7.0), 0.88 (3H, t, 7.5), $^{13}$C-NMR (125 MHz, Chloroform-d) $\delta_C$ ppm: 176.0, 168.8, 147.2, 136.9, 134.6, 100.9, 95.6, 61.9, 52.1, 41.7, 40.9, 39.0, 26.6, 16.5, 11.5, LRMS m/z 278.9 [M+H]$^+$.

Example 10. Preparation of Compound of Example 10 (((1S,4aS,5R,7aS)-8-oxo-1,4a,5,7a-tetrahydro-1,5-(epoxymethano)cyclopenta[c]pyran-3-yl)methyl 4-methyl benzoate)

The synthesis method was the same as the synthesis method of the compound of Example 4, but Compound of Example 10 was obtained using p-toluoyl chloride (0.052 mmol) instead of 4-bromobenzoyl chloride (FIG. 15). $^{1}$H-NMR (500 MHz, Chloroform-d) $\delta_H$ ppm (J, Hz): 7.93 (2H, d, 8.0), 7.22 (2H, d, 8.0), 6.38 (1H, dd, 5.5, 3.0), 6.35 (1H, dd, 5.5, 3.0), 5.78 (1H, br s), 5.33 (1H, d, 5.5), 4.76 (2H, d, 13.5), 3.34 (1H, br dd, 3.5), 2.99 (1H, br dd, 5.0), 2.74 (1H, br dd), 2.38 (3H, s), $^{13}$C-NMR (125 MHz, Chloroform-d) $\delta_C$ ppm: 168.8, 165.9, 147.1, 143.9, 136.9, 134.6, 129.7, 129.7, 129.1, 129.1, 126.8, 100.8, 95.6, 62.4, 52.1, 41.7, 39.0, 21.6, LRMS m/z 312.9 [M+H]$^+$.

Example 11. Preparation of Compound of Example 11 (((1S,4aS,5R,7aS)-8-oxo-1,4a,5,7a-tetrahydro-1,5-(epoxymethano)cyclopenta[c]pyran-3-yl)methyl 4-methoxybenzoate)

The synthesis method was the same as the synthesis method of the compound of Example 4, but Compound of Example 11 was obtained using 4-methoxybenzoyl chloride (0.052 mmol) instead of 4-bromobenzoyl chloride (FIG. 16). $^{1}$H-NMR (500 MHz, Chloroform-d) $\delta_H$ ppm (J, Hz): 7.99 (2H, d, 8.5), 6.90 (2H, d, 8.5), 6.38 (1H, dd, 5.5, 3.0), 6.24 (1H, dd, 5.5, 3.0), 5.77 (1H, br s), 5.32 (1H, d, 5.5), 4.74 (2H, d, 13.5), 3.82 (3H, s), 3.33 (1H, br dd, 5.5), 2.99 (1H, br dd, 5.0), 2.74 (1H, br dd), $^{13}$C-NMR (125 MHz, Chloroform-d) $\delta_C$ ppm: 168.8, 165.5, 163.5, 147.2, 136.9, 134.6, 131.7, 131.7, 121.9, 113.6, 113.6, 100.7, 95.6, 62.3, 55.4, 52.1, 41.7, 39.0, LRMS m/z 328.9 [M+H]$^+$.

Example 12. Preparation of Compound of Example 12 (((1S,4aS,5R,7aS)-8-oxo-1,4a,5,7a-tetrahydro-1,5-(epoxymethano)cyclopenta[c]pyran-3-yl)methyl [1,1'-biphenyl]-4-carboxylate)

The synthesis method was the same as the synthesis method of the compound of Example 4, but Compound of Example 12 was obtained using biphenyl-4-carbonyl chloride (0.052 mmol) instead of 4-bromobenzoyl chloride (FIG. 17). $^{1}$H-NMR (600 MHz, Chloroform-d) $\delta_H$ ppm (J, Hz): 8.13 (2H, d, 8.4), 7.67 (2H, d, 8.4), 7.62 (2H, d, 7.2), 7.47 (2H, t, 7.2), 7.40 (1H, t, 7.2), 6.41 (1H, dd, 6.0, 3.0), 6.39 (1H, dd, 6.0, 3.0), 5.82 (1H, br s), 5.39 (1H, d, 5.4), 4.84, 4.81 (2H, d, 13.2), 3.37 (1H, br dd, 4.0), 3.03 (1H, br dd, 4.5), 2.78 (1H, br dd), $^{13}$C-NMR (150 MHz, Chloroform-d) $\delta_C$ ppm: 168.9, 165.9, 147.2, 146.0, 140.0, 137.1, 134.6, 130.1, 130.1, 128.9, 128.9, 128.4, 128.2, 127.3, 127.3, 127.1, 127.1, 101.0, 95.7, 62.7, 52.2, 41.8, 39.1, LRMS m/z 397.1 [M+Na]$^+$.

Example 13. Preparation of Compound of Example 13 (((1S,4aS,5R,7aS)-8-oxo-1,4a,5,7a-tetrahydro-1,5-(epoxymethano)cyclopenta[c]pyran-3-yl)methyl 2-naphthoate)

The synthesis method was the same as the synthesis method of the compound of Example 4, but Compound of Example 13 was obtained using 2-naphthoyl chloride (0.052 mmol) instead of 4-bromobenzoyl chloride (FIG. 18). $^{1}$H-NMR (600 MHz, Chloroform-d) $\delta_H$ ppm (J, Hz): 8.63 (1H, s), 8.07 (1H, d, 7.8), 7.97 (1H, d, 7.8), 7.89 (1H, d, 8.4), 7.87 (1H, d, 8.4), 7.59 (1H, t, 7.8), 7.54 (1H, t, 7.8), 6.41 (1H, dd, 6.0, 3.6), 6.38 (1H, dd, 5.4, 3.0), 5.82 (1H, br s), 5.40 (1H, d, 5.4), 4.88, 4.85 (2H, d, 13.8), 3.38 (1H, br dd, 4.2), 3.03 (1H, br dd, 4.8), 2.78 (1H, br dd), $^{13}$C-NMR (150 MHz, Chloroform-d) $\delta_C$ ppm: 168.9, 166.1, 147.2, 137.0, 135.6, 134.6, 132.4, 131.4, 129.4, 128.4, 128.2, 127.7, 126.8, 126.7, 125.2, 101.1, 95.7, 62.8, 52.2, 41.8, 39.1, LRMS m/z 371.3 [M+Na]$^+$.

Example 14. Preparation of Compound of Example 14 (((1S,4aS,5R,7aS)-8-oxo-1,4a,5,7a-tetrahydro-1,5-(epoxymethano)cyclopenta[c]pyran-3-yl)methyl propiolate)

10.8 mg (0.052 mmol) of N,N'-dicyclohexylcarbodiimide and 4-dimethylaminopyridine (DMAP) in a catalytic amount were dissolved in 300 μL of dichloromethane, and then slowly injected in 300 μL of dichloromethane dissolved with Compound 1 (10 mg, 0.052 mmol) and 3.5 μL (0.052 mmol) of propiolic acid at 0° C. Thereafter, the mixture was stirred and reacted for 2 hours, and the reaction was completed by checking TLC. The obtained mixture was separated and purified to a desired result product using silica column chromatography (hexane:ethyl acetate=3:1, volume ratio) and HPLC (10% ACN to 100% ACN, 1 ml flow, 1 hr, ODS analytical column) to obtain Compound of Example 14 (FIG. 19). $^{1}$H-NMR (600 MHz, Chloroform-d) $\delta_H$ ppm (J, Hz): 6.40 (1H, dd, 5.4, 3.0), 6.37 (1H, dd, 6.0, 3.0), 5.79 (1H, br s), 5.34 (1H, d, 6.0), 4.67, 4.64 (2H, d, 13.2), 3.35 (1H, br dd, 3.0), 3.02 (1H, br dd, 5.4), 2.93 (1H, s), 2.75 (1H, br dd), $^{13}$C-NMR (150 MHz, Chloroform-d) $\delta_C$ ppm: 168.7, 152.0, 146.0, 137.0, 134.5, 102.3, 95.7, 75.8, 74.1, 63.8, 52.0, 41.7, 38.9, LRMS m/z 269.1 [M+Na]$^+$.

Example 15. Preparation of Compound of Example 15 ((1S,4aS,5R,7aS)-3-((E)-(prop-2-yn-1-ylimino)methyl)-1,4a,5,7a-tetrahydro-1,5-(epoxymethano)cyclopenta[c]pyran-8-one)

The compound (10 mg, 0.052 mmol) of Example 6 was dissolved in 300 μL of dichloromethane, and 6 mg (0.026 mmol) of trichloroisocyanuric acid was slowly injected into the solution dissolved in 300 μL of dichloromethane. After stirring for 30 minutes, 10 μL (0.156 mmol) of propargylamine dissolved in 100 μL of dichloromethane was added and reacted at room temperature for 5 hours. After completion of the reaction, all unreacted products were removed through vacuum drying, and the result product was separated and purified using filtration to obtain Compound of Example 15 (FIG. 20). $^{1}$H-NMR (600 MHz, Chloroform-d) 6H ppm (J, Hz): 8.03 (1H, s), 6.42 (1H, dd, 6.0, 3.0), 6.39 (1H, dd, 6.0, 3.0), 5.92 (1H, br s), 5.74 (1H, d, 6.0), 4.50 (1H, br s), 3.41 (1H, br dd, 3.0), 3.16 (1H, br dd, 5.4), 2.82 (1H, br dd), 2.52 (1H, br t, 2.4), $^{13}$C-NMR (150 MHz, Chloroform-d) $\delta_C$ ppm: 185.0, 168.4, 155.8, 147.8, 136.9, 134.5, 111.1, 95.8, 77.6, 52.0, 46.4, 42.3, 39.1, LRMS m/z 230.1 [M+H]$^+$.

Example 16. Preparation of Compound of Example 16 (((1S,4aS,5R,7aS)-8-oxo-1,4a,5,7a-tetrahydro-1,5-(epoxymethano)cyclopenta[c]pyran-3-yl)methyl 9-oxo-9H-fluorene-4-carboxylate)

The synthesis method was the same as the synthesis method of the compound of Example 4, but Compound of Example 16 was obtained using 9-fluorenone-4-carbonyl chloride (0.052 mmol) instead of 4-bromobenzoyl chloride (FIG. 21). $^{1}$H-NMR (600 MHz, Chloroform-d) $\delta_H$ ppm (J, Hz): 8.27 (1H, d, 7.8), 7.98 (1H, d, 7.8), 7.83 (1H, d, 7.2), 7.70 (1H, d, 7.2), 7.52 (1H, t, 7.2), 7.37 (1H, t, 7.8), 7.35 (1H, t, 7.2), 6.41 (1H, dd, 5.4, 3.0), 6.39 (1H, dd, 6.0, 3.0), 5.82 (1H, s), 5.42 (1H, d, 6.0), 4.92, 4.86 (2H, d, 12.6), 3.38 (1H, br dd, 3.6), 3.04 (1H, br dd, 4.8), 2.78 (1H, br dd), $^{13}$C-NMR (150 MHz, Chloroform-d) $\delta_C$ ppm: 192.9, 168.7, 166.1, 146.8, 144.3, 143.0, 137.1, 136.3, 135.6, 135.2, 134.6, 134.4, 129.9, 128.8, 127.5, 126.3, 126.3, 124.1, 102.0, 95.8, 63.4, 52.2, 41.8, 39.0, LRMS m/z 423.0 $[M+Na]^+$.

Example 17. Preparation of Compound of Example 17 (((1S,4aS,5R,7aS)-8-oxo-1,4a,5,7a-tetrahydro-1,5-(epoxymethano)cyclopenta[c]pyran-3-yl)methyl benzofuran-2-carboxylate)

The synthesis method was the same as the synthesis method of the compound of Example 4, but Compound of Example 17 was obtained using benzofuran-2-carbonyl chloride (0.052 mmol) instead of 4-bromobenzoyl chloride (FIG. 22). $^1$H-NMR (600 MHz, Chloroform-d) $\delta_H$ ppm (J, Hz): 7.68 (1H, d, 7.8), 7.59 (1H, d, 7.8), 7.58 (1H, s), 7.45 (1H, t, 7.8), 7.30 (1H, t, 7.8), 6.40 (1H, dd, 5.4, 3.0), 6.37 (1H, dd, 5.4, 3.0), 5.81 (1H, br s), 5.40 (1H, d, 5.4), 4.87, 4.82 (2H, d, 13.2), 3.37 (1H, br dd, 4.2), 3.02 (1H, br dd, 5.4), 2.77 (1H, br dd), $^{13}$C-NMR (150 MHz, Chloroform-d) $\delta_C$ ppm: 168.8, 158.9, 155.9, 146.6, 144.8, 137.0, 134.6, 127.8, 126.8, 123.8, 122.9, 114.7, 112.4, 101.8, 95.7, 62.9, 52.1, 41.7, 39.0, LRMS m/z 361.2 $[M+Na]^+$.

Example 18. Preparation of Compound of Example 18 (((1S,4aS,5R,7aS)-8-oxo-1,4a,5,7a-tetrahydro-1,5-(epoxymethano)cyclopenta[c]pyran-3-yl)methyl 4-fluorobenzoate)

The synthesis method was the same as the synthesis method of the compound of Example 4, but Compound of Example 18 was obtained using 4-fluorobenzoyl chloride (0.052 mmol) instead of 4-bromobenzoyl chloride (FIG. 23). $^1$H-NMR (600 MHz, Chloroform-d) $\delta_H$ ppm (J, Hz): 8.07 (1H, d, 8.4), 8.05 (1H, d, 8.4), 7.11 (1H, d, 8.4), 7.09 (1H, d, 8.4), 6.40 (1H, dd, 6.0, 3.0), 6.37 (1H, dd, 5.4, 3.6), 5.79 (1H, br s), 5.35 (1H, d, 6.0), 4.80, 4.75 (2H, d, 13.2), 3.35 (1H, br dd, 4.2), 3.01 (1H, br dd, 5.4), 2.75 (1H, br dd), $^{13}$C-NMR (150 MHz, Chloroform-d) $\delta_C$ ppm: 168.8, 166.7, 165.0, 147.0, 137.0, 134.6, 132.4, 132.3, 125.8, 155.7, 155.5, 101.4, 95.7, 62.8, 52.1, 41.7, 39.0, LRMS m/z 339.1 $[M+Na]^+$.

Example 19. Preparation of Compound of Example 19 (((1S,4aS,5R,7aS)-8-oxo-1,4a,5,7a-tetrahydro-1,5-(epoxymethano)cyclopenta[c]pyran-3-yl)methyl 4-chlorobenzoate)

The synthesis method was the same as the synthesis method of the compound of Example 4, but Compound of Example 19 was obtained using 4-chlorobenzoyl chloride (0.052 mmol) instead of 4-bromobenzoyl chloride (FIG. 24). $^1$H-NMR (600 MHz, Chloroform-d) $\delta_H$ ppm (J, Hz): 7.99 (2H, d, 9.0), 7.41 (2H, d, 9.0), 6.41 (1H, dd, 5.4, 3.0), 6.38 (1H, dd, 5.4, 3.0), 5.80 (1H, br s), 5.35 (1H, d, 6.0), 4.81, 4.76 (2H, d, 13.2), 3.36 (1H, br dd, 4.2), 3.02 (1H, br dd, 5.4), 2.76 (1H, br dd), $^{13}$C-NMR (150 MHz, Chloroform-d) $\delta_C$ ppm: 168.8, 165.1, 147.0, 139.7, 137.0, 134.6, 131.2, 131.2, 128.8, 128.8, 128.1, 101.5, 95.7, 63.0, 52.2, 41.8, 39.0, LRMS m/z 355.1 $[M+Na]^+$.

Example 20. Preparation of Compound of Example 20 (((1S,4aS,5R,7aS)-8-oxo-1,4a,5,7a-tetrahydro-1,5-(epoxymethano)cyclopenta[c]pyran-3-yl)methyl 4-iodobenzoate)

The synthesis method was the same as the synthesis method of the compound of Example 4, but Compound of Example 20 was obtained using 4-iodobenzoyl chloride (0.052 mmol) instead of 4-bromobenzoyl chloride (FIG. 25). $^1$H-NMR (600 MHz, Chloroform-d) $\delta_H$ ppm (J, Hz): 7.80 (2H, d, 8.4), 7.76 (2H, d, 8.4), 6.41 (1H, dd, 5.4, 3.0), 6.38 (1H, dd, 5.4, 3.0), 5.79 (1H, br s), 5.35 (1H, d, 6.0), 4.81, 4.76 (2H, d, 13.2), 3.36 (1H, br dd, 4.2), 3.02 (1H, br dd, 5.4), 2.76 (1H, br dd), $^{13}$C-NMR (150 MHz, Chloroform-d) $\delta_C$ ppm: 168.8, 165.5, 147.0, 137.8, 137.8, 137.1, 134.6, 131.2, 131.2, 129.1, 101.5, 101.2, 95.7, 63.0, 52.2, 41.8, 39.0, LRMS m/z 447.0 $[M+Na]^+$.

Example 21. Preparation of Compound of Example 21 (((1S,4aS,5R,7aS)-8-oxo-1,4a,5,7a-tetrahydro-1,5-(epoxymethano)cyclopenta[c]pyran-3-yl)methyl 4-nitrobenzoate)

The synthesis method was the same as the synthesis method of the compound of Example 4, but Compound of Example 21 was obtained using 4-nitrobenzoyl chloride (0.052 mmol) instead of 4-bromobenzoyl chloride (FIG. 26). $^1$H-NMR (600 MHz, Chloroform-d) $\delta_H$ ppm (J, Hz): 8.28 (2H, d, 9.0), 8.21 (2H, d, 9.0), 6.41 (1H, dd, 5.4, 3.0), 6.38 (1H, dd, 5.4, 3.0), 5.80 (1H, br s), 5.41 (1H, d, 5.4), 4.87, 4.80 (2H, d, 13.2), 3.37 (1H, br dd, 4.2), 3.04 (1H, br dd, 5.4), 2.77 (1H, br dd), $^{13}$C-NMR (150 MHz, Chloroform-d) $\delta_C$ ppm: 168.7, 164.1, 150.7, 146.6, 137.0, 135.0, 134.6, 130.9, 130.9, 123.6, 123.6, 102.4, 95.7, 63.6, 52.1, 41.8, 38.9, LRMS m/z 366.1 $[M+Na]^+$.

Example 22. Preparation of Compound of Example 22 ((1S,4aS,5R,7aS)-3-(iodomethyl)-1,4a,5,7a-tetrahydro-1,5-(epoxymethano)cyclopenta[c]pyran-8-one)

The compound (10 mg, 0.052 mmol) of Example 1 was dissolved in 300 μL of dichloromethane, and then stirred and reacted at room temperature for 10 minutes by adding 3.6 mg (0.052 mmol) of imidazole, 13.7 mg (0.052 mmol) of triphenylphosphine, and 13.2 mg (0.052 mmol) of iodine. The obtained mixture was separated and purified to a desired result product using silica column chromatography (hexane: ethyl acetate=3:1, volume ratio) to obtain Compound of Example 22 (FIG. 27). $^1$H-NMR (500 MHz, Chloroform-d) $\delta_H$ ppm (J, Hz): 6.38 (1H, dd, 5.5, 3.0), 6.31 (1H, dd, 5.5, 3.0), 5.77 (1H, br s), 5.35 (1H, d, 6.0), 3.80, 3.76 (2H, d, 10.5), 3.29 (1H, br dd, 3.0), 2.96 (1H, br dd, 5.0), 2.72 (1H, br dd), $^{13}$H-NMR (125 MHz, Chloroform-d) $\delta_C$ ppm: 168.6, 149.0, 136.7, 134.4, 100.0, 95.8, 51.5, 42.0, 38.8, 0.4, LRMS m/z 327.0 $[M+Na]^+$.

Examples 23 and 24. Preparation of Compound of Example 23 ((1S,4aS,5R,7aS)-3-(bromomethyl)-1,4a,5,7a-tetrahydro-1,5-(epoxymethano)cyclopenta[c]pyran-8-one) and Compound of Example 24 ((1S,4aS,5R,7aS)-4-bromo-3-(hydroxymethyl)-1,4a,5,7a-tetrahydro-1,5-(epoxymethano)cyclopenta[c]pyran-8-one)

The compound (10 mg, 0.052 mmol) of Example 1 was dissolved in 300 μL of dichloromethane, and then stirred and reacted at room temperature for 30 minutes by adding 3.6 mg (0.052 mmol) of imidazole, 13.7 mg (0.052 mmol) of triphenylphosphine, and 8.3 mg (0.052 mmol) of bromine. The obtained mixture was separated and purified to a desired result product using silica column chromatography (hexane: ethyl acetate=3:1, volume ratio) to obtain Compound of Example 23 and Compound of Example 24 (the yield of Compounds 23 and 24 was 7:3) (FIG. 28). Compound of Example 23: $^{1}$H-NMR (600 MHz, Chloroform-d) $\delta_H$ ppm (J, Hz): 6.40 (1H, dd, 5.4, 3.0), 6.37 (1H, dd, 6.0, 3.0), 5.82 (1H, br s), 5.36 (1H, d, 6.0), 3.88 (2H, s), 3.35 (1H, br dd), 3.02 (1H, br dd, 5.4), 2.76 (1H, br dd), $^{13}$H-NMR (150 MHz, Chloroform-d) $\delta_C$ ppm: 168.6, 148.2, 137.0, 134.5, 102.0, 95.9, 52.0, 42.1, 38.9, 29.0, LRMS m/z 380.0 $[M+Na]^+$. Compound of Example 24: $^{1}$H-NMR (600 MHz, Chloroform-d) $\delta_H$ ppm (J, Hz): 6.40 (2H, br s), 5.84 (1H, br s), 4.16, 4.06 (2H, d, 10.8), 3.55 (1H, br dd), 3.28 (1H, br dd, 4.8), 2.97 (1H, br dd), $^{13}$H-NMR (150 MHz, Chloroform-d) $\delta_C$ ppm: 166.8, 145.4, 136.6, 134.0, 99.3, 95.6, 50.8, 50.2, 40.7, 26.9, LRMS m/z 296.2 $[M+Na]^+$.

Example 25. Preparation of Compound of Example 25 ((1S,4aS,5R,7aS)-3-(chloromethyl)-1,4a,5,7a-tetrahydro-1,5-(epoxymethano)cyclopenta[c]pyran-8-one)

The compound (10 mg, 0.052 mmol) of Example 1 was dissolved in 300 μL of dimethyl sulfoxide (DMSO), and then stirred and reacted at room temperature for 6 hours by adding 7 μL (0.052 mmol) of trimethylchlorosilane (TMSCl). The obtained mixture was separated and purified to a desired result product using silica column chromatography (hexane:ethyl acetate=3:1, volume ratio) to obtain Compound of Example 25 (FIG. 29). $^{1}$H-NMR (600 MHz, Chloroform-d) $\delta_H$ ppm (J, Hz): 6.40 (1H, dd, 6.0, 3.6), 6.37 (1H, dd, 5.4, 3.0), 5.80 (1H, br s), 5.34 (1H, d, 5.4), 3.99 (2H, s), 3.34 (1H, br dd, 4.2), 3.02 (1H, br dd, 5.4), 2.75 (1H, br dd), $^{13}$C-NMR (150 MHz, Chloroform-d) $\delta_C$ ppm: 168.7, 147.9, 136.9, 134.5, 101.8, 95.8, 52.0, 42.4, 41.9, 38.9, LRMS m/z 235.1 $[M+Na]^+$.

The molecular weights of Compound of Example 1 and Compounds of Examples 2 to 25, which were semi-synthetic derivatives of Example 1, were shown in Table 2 below.

TABLE 2

| Compound | Structure | Molecular weight (MW) |
|---|---|---|
| Compound 1 | 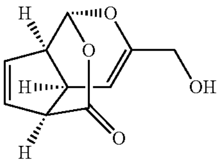 [SMILES: O=C1O[C@H]2OC(CO)=C[C@@H]3[C@H]2C=C[C@H]13] | 217.0 |
| Compound 2 | 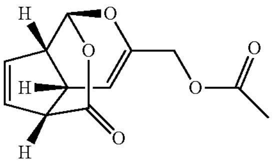 [SMILES: CC(=O)OCC1=C[C@H]2[C@@H]3C=C[C@H]2C(=O)O[C@@H]3O1] | 236.1 |
| Compound 3 | 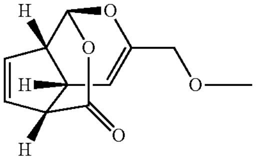 | 208.1 |
| Compound 4 | 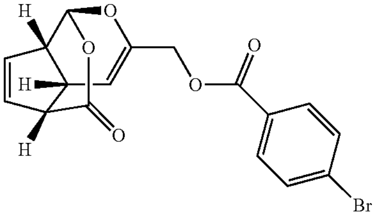 [SMILES: O=C(OCC1=C[C@H]2[C@@H]3C=C[C@H]2C(=O)O[C@@H]3O1)c1ccc(Br)cc1] | 376.2 |
| Compound 5 | 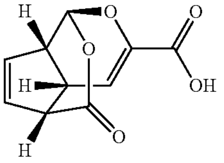 [SMILES: O=C(O)C1=C[C@H]2[C@@H]3C=C[C@H]2C(=O)O[C@@H]3O1] | 208.0 |

TABLE 2-continued
| Compound | Structure | Molecular weight (MW) |
| --- | --- | --- |
| Compound 6 | 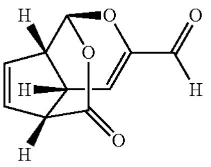 [SMILES: O=CC1=C[C@H]2[C@@H]3C=C[C@H]2C(=O)O[C@@H]3O1] | 192.2 |
| Compound 7 | 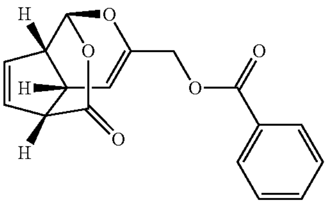 [SMILES: O=C(OCC1=C[C@H]2[C@@H]3C=C[C@H]2C(=O)O[C@@H]3O1)c1ccccc1] | 298.3 |
| Compound 8 | 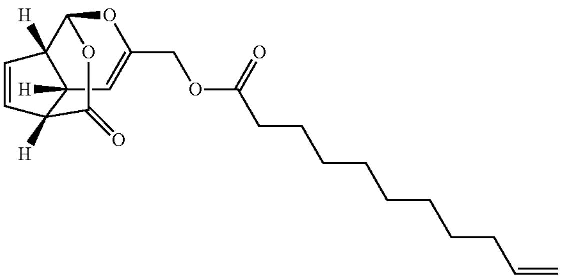 [SMILES: C=CCCCCCCCCC(=O)OCC1=C[C@H]2[C@@H]3C=C[C@H]2C(=O)O[C@@H]3O1] | 360.4 |
| Compound 9 | 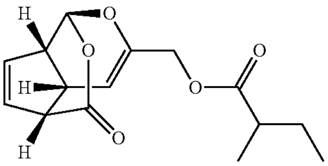 [SMILES: CCC(C)C(=O)OCC1=C[C@H]2[C@@H]3C=C[C@H]2C(=O)O[C@@H]3O1] | 278.2 |
| Compound 10 | 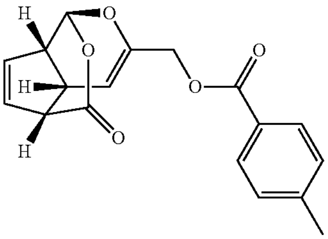 [SMILES: Cc1ccc(C(=O)OCC2=C[C@H]3[C@@H]4C=C[C@H]3C(=O)O[C@@H]4O2)cc1] | 312.3 |
| Compound 11 | 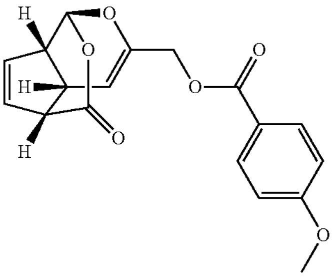 [SMILES: COc1ccc(C(=O)OCC2=C[C@H]3[C@@H]4C=C[C@H]3C(=O)O[C@@H]4O2)cc1] | 328.3 |

TABLE 2-continued
| Compound | Structure | Molecular weight (MW) |
|---|---|---|
| Compound 12 | 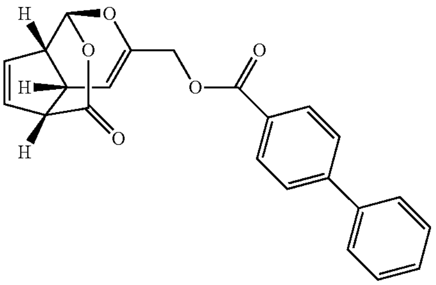 [SMILES: O=C(OCC1=C[C@H]2[C@@H]3C=C[C@H]2C(=O)O[C@@H]3O1)c1ccc(-c2ccccc2)cc1] | 374.4 |
| Compound 13 | 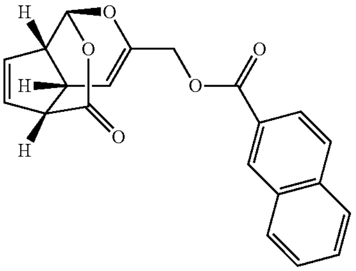 [SMILES: O=C(OCC1=C[C@H]2[C@@H]3C=C[C@H]2C(=O)O[C@@H]3O1)c1ccc2ccccc2c1] | 348.2 |
| Compound 14 | 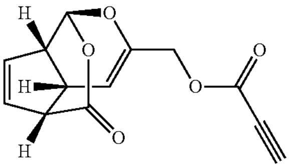 [SMILES: C#CC(=O)OCC1=C[C@H]2[C@@H]3C=C[C@H]2C(=O)O[C@@H]3O1] | 246.1 |
| Compound 15 | 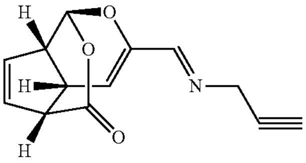 [SMILES: C#CC/N=C/C1=C[C@H]2[C@@H]3C=C[C@H]2C(=O)O[C@@H]3O1] | 229.0 |
| Compound 16 | 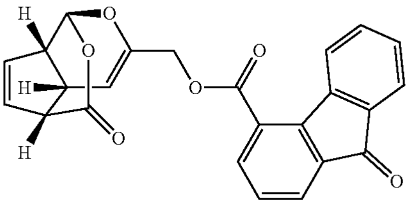 [SMILES: O=C(OCC1=C[C@H]2[C@@H]3C=C[C@H]2C(=O)O[C@@H]3O1)c1cccc2c1-c1ccccc1C2=O] | 400.3 |
| Compound 17 | 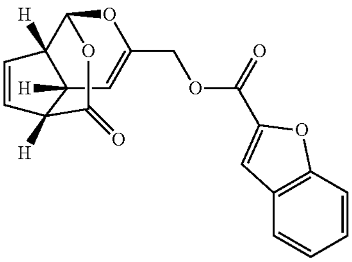 [SMILES: O=C(OCC1=C[C@H]2[C@@H]3C=C[C@H]2C(=O)O[C@@H]3O1)c1cc2ccccc2o1] | 338.4 |

TABLE 2-continued
| Compound | Structure | Molecular weight (MW) |
|---|---|---|
| Compound 18 | 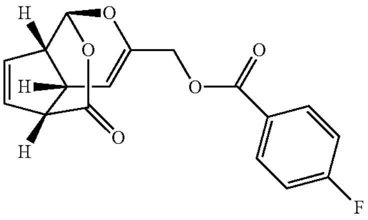 [SMILES: O=C(OCC1=C[C@H]2[C@@H]3C=C[C@H]2C(=O)O[C@@H]3O1)c1ccc(F)cc1] | 316.1 |
| Compound 19 | 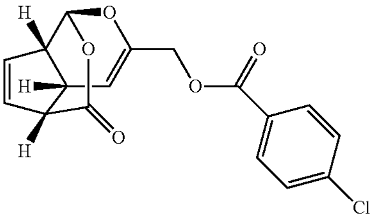 [SMILES: O=C(OCC1=C[C@H]2[C@@H]3C=C[C@H]2C(=O)O[C@@H]3O1)c1ccc(Cl)cc1] | 332.6 |
| Compound 20 | 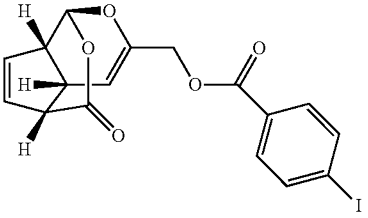 | 424.0 |
| Campound 21 | 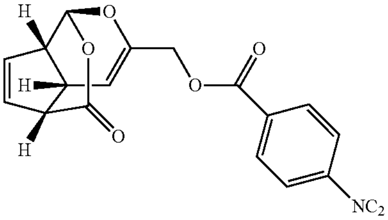 | 343.2 |
| Compound 22 | 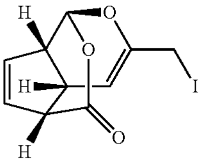 [SMILES: O=C1O[C@@H]2OC(CI)=C[C@H]3[C@@H]2C=C[C@@H]13] | 304.0 |
| Compound 23 | 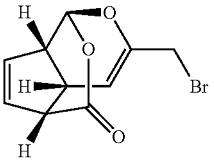 [SMILES: O=C1O[C@@H]2OC(CBr)=C[C@H]3[C@@H]2C=C[C@@H]13] | 257.1 |
| Compound 24 | 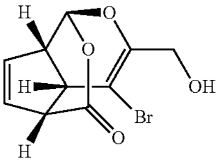 [SMILES: O=C1O[C@@H]2OC(CO)=C(Br)[C@H]3[C@@H]2C=C[C@@H]13] | 273.0 |

TABLE 2-continued

| Compound | Structure | Molecular weight (MW) |
|---|---|---|
| Compound 25 | 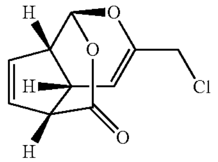 [SMILES: O=C1O[C@@H]2OC(CCl)=C[C@H]3[C@@H]2C=C[C@@H]13] | 212.4 |

Experimental Example

X-Ray Diffraction Analysis

Crystals of Compound 4 were coated with Paraton-N oil, and diffraction data were obtained using the Korea Pohang Accelerator. Data were collected using the PAL BL2D-SMDC program, and HKL3000sm was used for cell purification, reduction, and absorption correction. The crystal structure of Compound 4 was determined using a direct space method using the SELXT-2014/5 program, and the structure was analyzed using the SELXT-2014/7 program.

Culture of BV-2 Microglia Cells

BV-2 microglia cells were cultured in a humidified 5% $CO_2$ incubator at 37° C. using a Dulbecco's modified Eagle medium supplemented with 5% fetal bovine serum and 1% penicillin/streptomycin at 100 units/mL.

Experimental Example 1. Confirmation of Cytotoxicity and NO Production Inhibitory Effects In all experiments, the number of cells was 2.5×10$^5$ cell/ml, the cells were first treated with each of Compounds of Examples 1 to 25 by concentration (2.5 to 200 μg/ml), and LPS was diluted in medium and used at a concentration of 200 ng/ml. A cytotoxicity test was performed using MTT assay, and the MTT assay was performed by performing NO assay and injecting 30 μl of MTT at a concentration of 0.5 mg/ml into the cells in a microplate. After reacting for 2 hours in the incubator, formazan crystals were dissolved in 100 μl of DMSO, and the absorbance was measured using a Vmax microplate reader (Tencan Co., Switzerland) with a wavelength of 540 nm. In order to quantitatively measure the production of nitric oxide (NO), mouse BV-2 microglia cells were prepared in a microplate (96 well), and added with LPS (200 ng/ml) and Compounds by concentration (2.5 to 200 μg/ml). The cells reacted in an incubator for 24 h, and 50 μl of the supernatant reacted with a Griess reagent (a mixed solution of 1% sulfanilamide, 0.1% N-(1-naphthyl)-ethylenediamine dihydrochloride, and 2.5% $H_3PO_4$), and then the absorbance was measured using a Vmax 96-well microplate spectrophotometer with a wavelength of 550 nm.

(1) Confirmation of Cytotoxicity and NO Production Inhibitory Effects of Compound of Example 1 in Microglia Cells Stimulated with BV-2 LPS In order to analyze the anti-inflammatory efficacy of Compound of Example 1, the concentration inhibitory effect of nitric oxide (NO) produced in mouse BV-2 microglia cells stimulated with LPS (200 ng/ml), a neuroinflammatory factor, was confirmed. As a result of treating the extract at 20 to 60 μM, it was confirmed that the amount of nitric oxide (NO) was reduced as shown in FIG. 30A, and the detailed NO production inhibitory effect was shown in Table 3 below.

(2) Confirmation of Cytotoxicity and NO Production Inhibitory Effects of Compounds of Examples 2 to 25 in Microglia Cells Stimulated with BV-2 LPS The neuroinflammation inhibitory effects of Compounds of Examples 2 to 25 were confirmed. Using the same method as above, experiments were conducted at concentrations (1.25 to 200 μM) that did not show cytotoxicity. As a result, it was confirmed that NO production was noticeably inhibited as shown in FIGS. 31A, 31C, 32A, 32C, 33A, and 34B. Among them, the $IC_{50}$ values of Compounds 4, 6, 14, 15, 16, and 19 were confirmed as 13.3, 4.5, 1.4, 12.4, 3.8, and 14.5 μM, respectively, which was 3 to 33 times higher than the NO inhibitory effect (46.6 μM) of Compound 1 isolated as a natural product. The detailed NO production inhibitory effect was shown in Table 3 below.

TABLE 3

| Compound | NO inhibitory activity ($IC_{50\ value}$, μM) |
|---|---|
| Example 1 | 46.6 |
| Example 2 | >20 |
| Example 3 | >20 |
| Example 4 | 13.3 |
| Example 5 | >20 |
| Example 6 | 4.5 |
| Compound 7 | >20 |
| Compound 8 | >20 |
| Compound 9 | >20 |
| Compound 10 | >20 |
| Compound 11 | >20 |
| Compound 12 | >20 |
| Compound 13 | >20 |
| Compound 14 | 1.4 |
| Compound 15 | 12.4 |
| Compound 16 | 3.8 |
| Compound 17 | >20 |
| Compound 18 | >20 |
| Compound 19 | 14.5 |
| Compound 20 | >20 |
| Compound 21 | >20 |
| Compound 22 | >20 |
| Compound 23 | >20 |
| Compound 24 | <20 |
| Compound 25 | >20 |

Experimental Example 2. Confirmation of Expression Inhibitory Effect of iNOS and COX-2

To determine changes in expression patterns of inducible nitric oxide synthase (iNOS) and cyclooxygenase type 2 (COX-2) proteins and genes, which were enzymes involved in inflammation, BV-2 cells were treated with LPS (200 ng/ml), Compound of Example 1, and Compound of Example 4 and Compound of Example 6, which had showed strong inhibitory effect, by concentration (2 to 80 μg/ml), and cultured in a 6-well plate. After culturing for 18 hours, the proteins were identified, and the expression patterns of iNOS and COX-2 proteins were confirmed by performing Western blot using polyclonal antibodies to iNOS and COX-2. For 6 hours after culturing the BV-2 cells by setting the same conditions, the cell supernatant was removed, RNA was identified from the cells, and iNOS and COX-2 genes were analyzed by RT-PCR. As a result, as shown in FIGS. 30(*c*), 35(*c*), and 36(*c*), it could be confirmed that natural product Compound 1 and derivative Compounds 4 and 6 decreased the expression levels of iNOS and COX-2 proteins and genes in a concentration-dependent manner.

Experimental Example 3. Confirmation of Inhibitory Effect on Production of Inflammation-Mediated Cytokines In order to derive changes in the expression pattern of inflammation-mediated cytokines TNF-α, IL1-β, and IL-6 genes, BV-2 microglia cells were disposed in a 6-well plate and cultured for 24 hours, and pretreated for 1 hour with Compound of Example 1 and Compound of Example 6, which had showed strong inhibitory effect, by concentration (2 to 80 μg/ml). Then, the cells were stimulated with LPS (200 ng/ml). After 6 hours, the cell supernatant was removed, RNA was identified from the cells, and TNF-α, IL1-β, and IL-6 genes were analyzed by RT-PCR. As a result, as shown in FIGS. 30(*d*), 35(*d*), and 36(*d*), it could be confirmed that natural product compound 1 and derivative compounds 4 and 6 decreased the expression levels of TNF-α, IL1-β, and IL-6 genes in a concentration-dependent manner.

Experimental Example 4. Confirmation of Cytotoxicity and NO Production Inhibitory Effects of Compound 26 of Chemical Formula 2 in Microglia Cells Stimulated with BV-2 LPS In order to analyze the anti-inflammatory efficacy of Compound 26 of Chemical Formula 2, the concentration inhibitory effect of nitric oxide (NO) produced in mouse BV-2 microglia cells stimulated with LPS (200 ng/ml), a neuroinflammatory factor, was confirmed. Compound 26 of Chemical Formula 2 was purchased from Santa Cruz biotechnology (CAS 79127-35-8) and the experiment was performed. As a result of treating Compound of Chemical Formula 2 at 2.5 to 20 PM, it was confirmed that the amount of nitric oxide (NO) was reduced, as shown in FIG. 37A.

As described above, the present invention has been described through Examples. Those skilled in the art will be able to understand that the present invention may be easily executed in other detailed forms without changing the technical spirit or an essential feature thereof. Therefore, it is to be understood that the above-described embodiments are illustrative and not restrictive in all respects. The scope of the present invention is represented by claims to be described below rather than the detailed description, and it is to be interpreted that the meaning and scope of the claims and all the changes or modified forms derived from the equivalents thereof come within the scope of the present invention.

Accession Number

Depositary Authority Name: Korea Research Institute of Bioscience and Biotechnology Accession number: KCTCT4126BP Accession Date: 20200205.

Receipt in the case of an original issued pursuant to Rule 7.1 by the international depositary authority identified at the bottom of this page.

Depositor: Korea Institute of Ocean Science & Technology

385, Haeyangro, Youngdogu, Pusansi, Republic of Korea

I. IDENTIFICATION OF THE MICROORGANISM

| IDENTIFICATION FOR DISTINGUISH GIVEN BY DEPOSITOR: | ACCESSION NUMBER GIVEN BY INTERNATIONAL DEPOSITARY |
|---|---|
| *Streptomyces malaysiense* 151KO-065 | INSTITUTION: KCTC14126BP |

II. SCIENTIFIC DESCRIPTION AND/OR PROPOSED TAXONOMIC DESIGNATION

MICROORGANISM DESIGNATED IN IINCLUDES DOCUMENTS HAVING FOLLOWING ITE MS

□SCIENTIFIC PROPERTY □PROPOSED TAXONOMIC DESIGNATION (Mark x where applicable)

III. RECEIPT AND DEPOSIT

This international depositary authority accepts the microorganism identified under I above, which was received by it on Feb. 5, 2020.

IV. RECEIPT OF CONVERSION REQUEST

The microorganism identified in I above has been received by the international depositary authority and a request has been received to convert the initial deposit to a deposit in accordance with the Budapest Treaty

V. INTERNATIONAL DEPOSITARY INSTITUTION

| | |
|---|---|
| NAME: Korean Collection for Type Cultures | SIGNATURE: YOUR SIGNATURE IN YOUR OWN HANDWRITING |
| ADDRESS: 181, Ipsingil, Jeongeupsi, Jeollabukdo, Republic of Korea, 56212 | SIGNATURE: |
| | DATE: Feb. 5, 2020 |

The invention claimed is:

1. A compound of Chemical Formula 1 below, an optical isomer thereof or a pharmaceutically acceptable salt thereof:

[Chemical Formula 1]

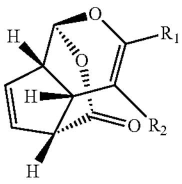

In Chemical Formula 1 above, $R_1$ is —C(═O)$R_a$, —$CH_2R_b$ or —CH═$NCH_2C$≡CH, $R_a$ is any one selected from the group consisting of —H, —OH, —$OCH_3$, —$OCH_2CH_3$, and —$OCH_2CH_2CH_3$, $R_b$ is —$OR_{b1}$ or halogen, $R_{b1}$ is any one selected from the group consisting of —H, straight-chain or branched-chain $C_1$-$C_5$alkyl, —C(═O)$R_{b11}$,

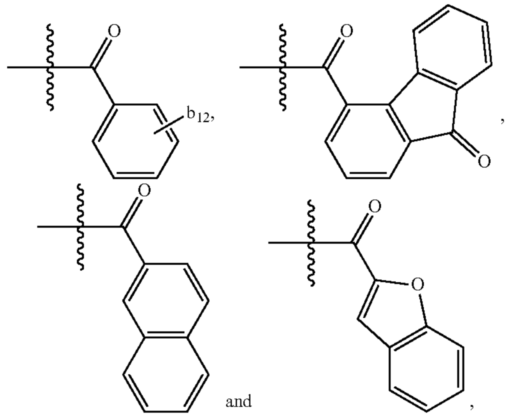

$R_{b11}$ is a straight-chain or branched-chain $C_1$-$C_8$alkyl group or a straight-chain or branched-chain $C_6$-$C_{12}$ alkenyl group containing at least one double or triple bond between carbons, $R_{b12}$ is any one selected from the group consisting of —H, —$CH_3$, —$CH_2CH_3$, —$CH_2CH_2CH_3$, halogen, —$OCH_3$ and —$OCH_2CH_3$, —$NO_2$ and a phenyl group, and $R_2$ is —H or halogen.

2. The compound, the optical isomer thereof or the pharmaceutically acceptable salt thereof of claim 1, wherein $R_1$ is —C(═O)$R_a$ and $R_a$ is —H or —OH.

3. The compound, the optical isomer thereof or the pharmaceutically acceptable salt thereof of claim 1, wherein $R_1$ is —$CH_2R_b$, $R_b$ is —$OR_{b1}$ or halogen, $R_{b1}$ is any one selected from the group consisting of —H, straight-chain or branched-chain $C_1$-$C_5$alkyl, —C(═O)$R_{b11}$,

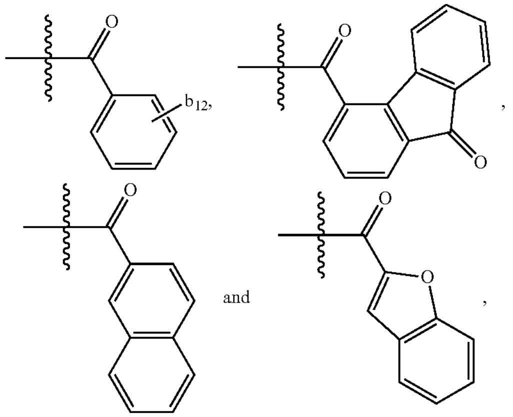

$R_{b11}$ is a straight-chain or branched-chain $C_1$-$C_8$alkyl group or straight-chain or branched-chain $C_6$ to $C_{12}$ alkenyl group including one or more double or triple bonds between carbons, $R_{b12}$ is any one selected from the group consisting of —H, —$CH_3$, —$CH_2CH_3$, —$CH_2CH_2CH_3$, halogen, —$OCH_3$ and —$OCH_2CH_3$, —$NO_2$ and a phenyl group, and $R_2$ is —H or halogen.

4. The compound, the optical isomer thereof or the pharmaceutically acceptable salt thereof of claim 3, wherein Rbi is any one selected from the group consisting of —H, -straight-chain or branched-chain $C_1$-$C_3$ alkyl, —C(═O)$R_{b11}$,

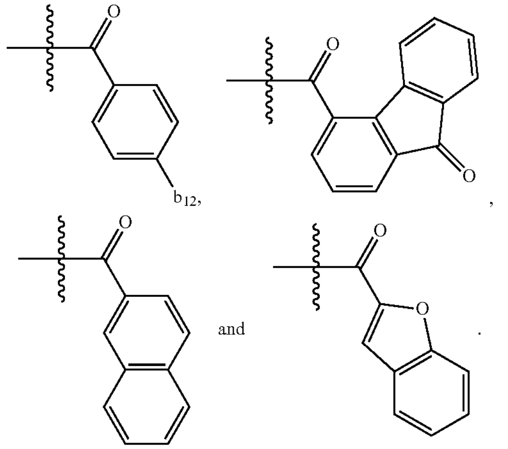

5. The compound, the optical isomer thereof or the pharmaceutically acceptable salt thereof of claim 3, wherein $R_{b11}$ is any one selected from the group consisting of —$CH_3$,

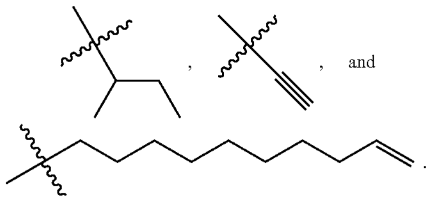

6. The compound, the isomer thereof or the pharmaceutically acceptable salt thereof of claim 1, wherein the compound of Chemical Formula 1 is any one selected from the group consisting of the following compounds:

(1S,4aS,5R,7aS)-3-(hydroxymethyl)-1,4a,5,7a-tetrahydro-1,5-(epoxymethano)cyclopenta[c]pyran-8-one;

((1S,4aS,5R,7aS)-8-oxo-1,4a,5,7a-tetrahydro-1,5-(epoxymethano)cyclopenta[c]pyran-3-yl)methyl acetate;

(1S,4aS,5R,7aS)-3-(methoxymethyl)-1,4a,5,7a-tetrahydro-1,5-(epoxymethano)cyclopenta[c]pyran-8-one;

((1S,4aS,5R,7aS)-8-oxo-1,4a,5,7a-tetrahydro-1,5-(epoxymethano)cyclopenta[c]pyran-3-yl)methyl 4-bromobenzoate;

(1S,4aS,5R,7aS)-8-oxo-1,4a,5,7a-tetrahydro-1,5-(epoxymethano)cyclopenta[c]pyran-3-carboxylic acid;

(1S,4aS,5R,7aS)-8-oxo-1,4a,5,7a-tetrahydro-1,5-(epoxymethano)cyclopenta[c]pyran-3-carbaldehyde;

((1S,4aS,5R,7aS)-8-oxo-1,4a,5,7a-tetrahydro-1,5-(epoxymethano)cyclopenta[c]pyran-3-yl)methyl benzoate;

((1S,4aS,5R,7aS)-8-oxo-1,4a,5,7a-tetrahydro-1,5-(epoxymethano)cyclopenta[c]pyran-3-yl)methylundec-10-enoate;

((1S,4aS,5R,7aS)-8-oxo-1,4a,5,7a-tetrahydro-1,5-(epoxymethano)cyclopenta[c]pyran-3-yl)methyl 2-methyl butanoate;

((1S,4aS,5R,7aS)-8-oxo-1,4a,5,7a-tetrahydro-1,5-(epoxymethano)cyclopenta[c]pyran-3-yl)methyl 4-methyl benzoate;

((1S,4aS,5R,7aS)-8-oxo-1,4a,5,7a-tetrahydro-1,5-(epoxymethano)cyclopenta[c]pyran-3-yl)methyl 4-methoxybenzoate;

((1S,4aS,5R,7aS)-8-oxo-1,4a,5,7a-tetrahydro-1,5-(epoxymethano)cyclopenta[c]pyran-3-yl)methyl [1,1'-biphenyl]-4-carboxylate;

((1S,4aS,5R,7aS)-8-oxo-1,4a,5,7a-tetrahydro-1,5-(epoxymethano)cyclopenta[c]pyran-3-yl)methyl 2-naphthoate;

((1S,4aS,5R,7aS)-8-oxo-1,4a,5,7a-tetrahydro-1,5-(epoxymethano)cyclopenta[c]pyran-3-yl)methyl propiolate;

(1S,4aS,5R,7aS)-3-((E)-(prop-2-yn-1-ylimino)methyl)-1,4a,5,7a-tetrahydro-1,5-(epoxymethano)cyclopenta[c]pyran-8-one;

((1S,4aS,5R,7aS)-8-oxo-1,4a,5,7a-tetrahydro-1,5-(epoxymethano)cyclopenta[c]pyran-3-yl)methyl 9-oxo-9H-fluorene-4-carboxylate;

((1S,4aS,5R,7aS)-8-oxo-1,4a,5,7a-tetrahydro-1,5-(epoxymethano)cyclopenta[c]pyran-3-yl)methyl benzofuran-2-carboxylate;

((1S,4aS,5R,7aS)-8-oxo-1,4a,5,7a-tetrahydro-1,5-(epoxymethano)cyclopenta[c]pyran-3-yl)methyl 4-fluorobenzoate;

((1S,4aS,5R,7aS)-8-oxo-1,4a,5,7a-tetrahydro-1,5-(epoxymethano)cyclopenta[c]pyran-3-yl)methyl 4-chlorobenzoate;

((1S,4aS,5R,7aS)-8-oxo-1,4a,5,7a-tetrahydro-1,5-(epoxymethano)cyclopenta[c]pyran-3-yl)methyl 4-iodobenzoate;

((1S,4aS,5R,7aS)-8-oxo-1,4a,5,7a-tetrahydro-1,5-(epoxymethano)cyclopenta[c]pyran-3-yl)methyl 4-nitrobenzoate;

(1S,4aS,5R,7aS)-3-(iodomethyl)-1,4a,5,7a-tetrahydro-1,5-(epoxymethano)cyclopenta[c]pyran-8-one;

(1S,4aS,5R,7aS)-3-(bromomethyl)-1,4a,5,7a-tetrahydro-1,5-(epoxymethano)cyclopenta[c]pyran-8-one;

(1S,4aS,5R,7aS)-4-bromo-3-(hydroxymethyl)-1,4a,5,7a-tetrahydro-1,5-(epoxymethano)cyclopenta[c]pyran-8-one; and (1S,4aS,5R,7aS)-3-(chloromethyl)-1,4a,5,7a-tetrahydro-1,5-(epoxymethano)cyclopenta[c]pyran-8-one.

7. A pharmaceutical composition comprising a compound represented by Chemical Formula 1 below, an isomer thereof, or a pharmaceutically acceptable salt thereof as an active ingredient:

[Chemical Formula 1]

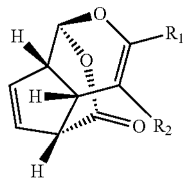

In Chemical Formula 1 above, $R_1$ is —C(=O)$R_a$, —$CH_2R_b$ or —CH=$NCH_2C$≡CH, $R_a$ is any one selected from the group consisting of —H, —OH, —$OCH_3$, —$OCH_2CH_3$, and —$OCH_2CH_2CH_3$, $R_b$ is —$OR_{b1}$ or halogen, $R_{b1}$ is any one selected from the group consisting of —H, —$CH_3$, —$CH_2CH_3$, —$CH_2CH_2CH_3$, —C(=O)$R_{b11}$,

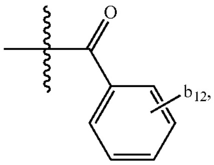 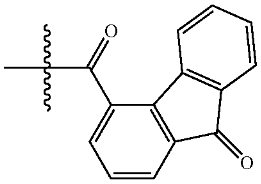 ,

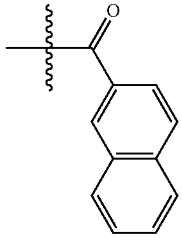 and 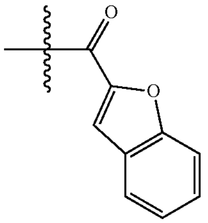 , $R_{b11}$ is a straight-chain or branched-chain $C_1$-$C_5$alkyl group or a straight-chain or branched-chain $C_6$-$C_{12}$ alkenyl group containing at least one double or triple bond between carbons, $R_{b12}$ is any one selected from the group consisting of —H, —$CH_3$, —$CH_2CH_3$, —$CH_2CH_2CH_3$, halogen, —$OCH_3$ and —$OCH_2CH_3$, —$NO_2$ and a phenyl group, and $R_2$ is —H or halogen.

* * * * *